(12) United States Patent
Bray et al.

(10) Patent No.: US 11,783,366 B2
(45) Date of Patent: Oct. 10, 2023

(54) COMBINATION THERAPIES

(71) Applicant: Genentech, Inc., South San Francisco, CA (US)

(72) Inventors: Gordon Bray, San Francisco, CA (US); Iris Chan, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 52 days.

(21) Appl. No.: 17/444,691

(22) Filed: Aug. 9, 2021

(65) Prior Publication Data

US 2022/0172244 A1 Jun. 2, 2022

Related U.S. Application Data

(63) Continuation of application No. 13/967,782, filed on Aug. 15, 2013, now Pat. No. 11,087,354.

(60) Provisional application No. 61/780,708, filed on Mar. 13, 2013, provisional application No. 61/722,725, filed on Nov. 5, 2012, provisional application No. 61/706,026, filed on Sep. 26, 2012, provisional application No. 61/705,575, filed on Sep. 25, 2012, provisional application No. 61/684,673, filed on Aug. 17, 2012.

(51) Int. Cl.
| | | |
|---|---|---|
| *A61K 31/397* | (2006.01) | |
| *A61K 31/375* | (2006.01) | |
| *A61P 17/00* | (2006.01) | |
| *A61P 35/00* | (2006.01) | |
| *A61P 35/04* | (2006.01) | |
| *G06Q 30/0241* | (2023.01) | |
| *A61K 31/437* | (2006.01) | |
| *C12Q 1/6886* | (2018.01) | |
| *A61K 31/4523* | (2006.01) | |

(52) U.S. Cl.
CPC ....... *G06Q 30/0241* (2013.01); *A61K 31/437* (2013.01); *A61K 31/4523* (2013.01); *C12Q 1/6886* (2013.01); *C12Q 2600/106* (2013.01)

(58) Field of Classification Search
CPC ..... A61K 31/397; A61K 31/375; A61P 17/00; A61P 35/00; A61P 35/04
USPC ............................................ 514/210.18, 300
See application file for complete search history.

(56) References Cited

U.S. PATENT DOCUMENTS

| | | |
|---|---|---|
| 7,144,907 B2 | 12/2006 | Wallace et al. |
| 7,307,071 B2 | 12/2007 | Lyons et al. |
| 7,378,423 B2 | 5/2008 | Kawasaki et al. |
| 7,491,829 B2 | 2/2009 | Laird et al. |
| 7,504,509 B2 | 3/2009 | Ibrahim et al. |
| 7,511,058 B2 | 3/2009 | Hurley et al. |
| 7,517,994 B2 | 4/2009 | Marlow et al. |
| 7,576,072 B2 | 8/2009 | Wallace et al. |
| 7,576,114 B2 | 8/2009 | Wallace et al. |
| 7,598,383 B2 | 10/2009 | Marlow et al. |
| 7,713,960 B2 | 5/2010 | Sebti |
| 7,803,839 B2 | 9/2010 | Aay et al. |
| 7,863,288 B2 | 1/2011 | Ibrahim et al. |
| 7,893,065 B2 | 2/2011 | Marlow et al. |
| 7,915,250 B2 | 3/2011 | Aay et al. |
| 7,973,170 B2 | 7/2011 | Wallace et al. |
| 7,994,185 B2 | 8/2011 | Rheault |
| 7,999,006 B2 | 8/2011 | Lamb |
| 8,003,805 B2 | 8/2011 | Wallace et al. |
| 8,101,611 B2 | 1/2012 | Marlow et al. |
| 8,101,639 B2 | 1/2012 | Marlow et al. |
| 8,143,271 B2 | 3/2012 | Ibrahim et al. |
| 8,178,693 B2 | 5/2012 | Wallace et al. |
| 8,211,921 B2 | 7/2012 | Blake et al. |
| 8,268,852 B2 | 9/2012 | Blake et al. |
| 8,394,795 B2 | 3/2013 | Ahrendt et al. |
| 8,415,345 B2 | 4/2013 | Adjabeng et al. |
| 8,426,418 B2 | 4/2013 | Coopersmith et al. |
| 8,431,574 B2 | 4/2013 | Blake et al. |
| 8,470,818 B2 | 6/2013 | Ibrahim et al. |
| 8,501,758 B2 | 8/2013 | Huang et al. |
| 8,580,304 B2 | 11/2013 | DeMarini et al. |
| 8,709,419 B2 | 4/2014 | Dhingra et al. |
| 11,087,354 B2 * | 8/2021 | Bray .................. C12Q 1/6886 |
| 2006/0216288 A1 | 9/2006 | Chang |
| 2008/0058340 A1 | 3/2008 | Maderna et al. |
| 2009/0075267 A1 | 3/2009 | Siena et al. |
| 2009/0156576 A1 | 6/2009 | Aay et al. |
| 2009/0202989 A1 | 8/2009 | Hillan et al. |
| 2010/0004253 A1 | 1/2010 | Aziz et al. |
| 2010/0249096 A1 | 9/2010 | Aay et al. |
| 2010/0260714 A1 | 10/2010 | Wallace et al. |
| 2010/0310659 A1 | 12/2010 | Desai et al. |

(Continued)

FOREIGN PATENT DOCUMENTS

| | | |
|---|---|---|
| WO | 2005047542 A1 | 5/2005 |
| WO | 2007002325 A1 | 1/2007 |

(Continued)

OTHER PUBLICATIONS

Ascierto et al., "The role of BRAF V600 mutation in melanoma", Journal of Translational Medicine, 2012, vol. 10, No. 85, 9 pages.
Bauday et al., "FDG-PET is a good biomarker of both early response and acquired resistance in BRAFV600 mutant melanomas treated with vemurafenib and the MEK inhibitor GDC-0973", EJNMMI Research 2, 2012, (Suppl 22), pp. 1-10.

(Continued)

*Primary Examiner* — Raymond J Henley, III
(74) *Attorney, Agent, or Firm* — Armstrong Teasdale LLP

(57) ABSTRACT

The present invention relates generally to the fields of molecular biology and growth factor regulation. More specifically, the invention relates to therapies for the treatment of pathological conditions, such as cancer.

15 Claims, 7 Drawing Sheets

(56) References Cited

U.S. PATENT DOCUMENTS

| | | |
|---|---|---|
| 2011/0003809 A1 | 1/2011 | Ahrendt |
| 2011/0086837 A1 | 4/2011 | Belvin et al. |
| 2011/0183981 A1 | 7/2011 | Marlow et al. |
| 2012/0045433 A1 | 2/2012 | Dhingra et al. |
| 2012/0136030 A1 | 5/2012 | Miner et al. |
| 2012/0148533 A1 | 6/2012 | Dhingra et al. |
| 2012/0202822 A1 | 8/2012 | Bachman et al. |
| 2012/0214828 A1 | 8/2012 | Hatzivassiliou et al. |
| 2013/0018075 A1 | 1/2013 | Marlow et al. |
| 2013/0059851 A1 | 3/2013 | Garraway et al. |
| 2013/0172375 A1 | 7/2013 | Albano et al. |
| 2013/0217710 A1 | 8/2013 | Alves-Aivado et al. |
| 2013/0217721 A1 | 8/2013 | Lo et al. |
| 2013/0231347 A1 | 9/2013 | Bleam et al. |
| 2013/0245039 A1 | 9/2013 | Higgins et al. |

FOREIGN PATENT DOCUMENTS

| | | |
|---|---|---|
| WO | 2007002433 A1 | 1/2007 |
| WO | 2008120004 A1 | 10/2008 |
| WO | 2009018238 A1 | 2/2009 |
| WO | 2009111277 A1 | 9/2009 |
| WO | 2009111278 A2 | 9/2009 |
| WO | 2009111279 A1 | 9/2009 |
| WO | 2009111280 A1 | 9/2009 |
| WO | 2010114928 A2 | 10/2010 |
| WO | 2011028540 A1 | 3/2011 |
| WO | 2011054620 A1 | 5/2011 |
| WO | 2011104694 A1 | 9/2011 |
| WO | 2012068562 A2 | 5/2012 |
| WO | 2012145503 A1 | 10/2012 |
| WO | 2012161776 A1 | 11/2012 |
| WO | 2014128235 A1 | 8/2014 |

OTHER PUBLICATIONS

Bollag et al. "Clinical efficacy of a RAFinhibitor needs broad target blockade in BRAF-mutant melanoma", Nature, 2010, vol. 467, No. 7315, pp. 596-599.
CAS Registry Database, 934660-93-2.
Catalog page for Bay-43-9006, 2 pages.
Center for Drag Evaluation and Research (CDER), "Guidance for Industry—Nonclinical Safety Evaluation of Drag or Biologic Combinations", Mar. 2006, Pharmacology and Toxicology, 16 pages.
Chapman et al., "Improved survival with Vemurafenib in melanoma with BRAF V600E mutation" New England Journal of Medicine 364(26):2507-2516 (Jun. 2011).
Chemical Abstracts Service, record for Registry No. 918504-65-1, accessed Apr. 2, 2015.
Cheng et al., "Current Development Status of MEK Inhibitors", Molecules, 2017, 22, 1551, 20 pgs.
Choo et al., "Preclinical Disposition of GDC-0973 and Prospective and Retrospective Analysis of Human Dose and Efficacy Predictions", Drug Metabolism and Disposition, 2012, vol. 40, No. 5, pp. 919-927.
ClinicalTrials.gov archive, "A Study Comparing Vemruafenib Versus Vemurafenib Plus Cobimetinib in Participants With Metastatic Melanoma", History of Change for Study: NCT01689519, https://www.clinicaltrials.gov/ct2/history/NCT01689519, Mar. 18, 2019, 13 pages.
Cobas 4800 BRAF V600 Mutation Test brochure, Roche Molecular Diagnostics, http://molecular.roche.eom/assays/Pages/cobas4800BRAFV600MutationTest.aspx, accessed Apr. 2, 2015.
Daud et al., "Indirect treatment comparison of dabrafenib plus trametinib versus vemurafenib plus cobimetinib in previously untreated metastatic melanoma patients", Journal of Hematology & Oncology, 2017, vol. 10, No. 3, 9 pages.
Eroglu et al., "Combination therapy with BRAF and MEK inhibitors for melanoma: latest evidence and place in therapy", Therapeutic Advances in Medical Oncology, 2016, vol. 8, No. 1, pp. 48-56.
Esteve-Puig et al., "Uncoupling of the LKB1-AMPKalpha energy sensor pathway by growth factors and oncogenic BRAF" PLoS One 4(3):e4771 (2009).
Flaherty et al., "Inhibition of mutated, activated BRAF in metastatic melanoma" N Engl J Med. 363(9):809-19 (2010).
Gild et al., "Multikinase inhibitors: a new option for the treatment of thyroid cancer" Nat Rev Endocrinol. 7(10):617-24 (2011).
Gonzalez et al., "Phase IB Study of Vemurafenib in Combinationwith the MEK Inhibitor, GDC-0973, in Patients (PTS) WithUnresectable orMetastic BRAFV600 Mutated Metastic Melanoma (BRIM7)", Annals of Oncology, 2012, vol. 23 (Supplement 9), 3 pages.
Guida et al., "Metastatic melanoma: the new era of targeted therapy", Expert Opinion on Therapeutic Targets, vol. 16, Supplement 2, pp. S61-S70.
Halait et al., "Analytical performance of a real-time PCR-bsed assay for V600 mutations in the BRAF gene, used as the companion diagnostic test for the novel BRAF inhibitor vemurafenib in metastatic melanoma" Diagnostic Molecular Pathology 21(1):1-8 (2012).
Hoffmann-La Roche Ltd., "Eine Doppelblinde, Placebokontrollierte Phase-III-Studie Zu Vemurafenib Versus Vemurafenib Plus GDC-0973 Bei Zuvor Unbehandelten Brafv600"—Mutation-Positiven Patienten Mit Nicht-Resezierbarem Lokal Fortgeschrittenem Oder Metastasiertem Melanom", Roche GO28141_Zusammenfassung des Studienprotokolls, Version 2 vom Sep. 26, 2012_DE, 13 pages.
Infante et al., "Phase I/II study to assess safety, pharmacokinetics, and efficacy of the oral MEK 1/2 inhibitor GSK1120212 (GSK212) dosed in combination with the oral BRAF inhibitor GSK2118436 (GSK436)." J Clin Onc (2011), abstr CRA 8503.
Infante et al., "Safety, pharmacokinetic, pharmacodynamic, and efficacy data for the oral MEK inhibitor trametinib: a phase 1 dose-escalation trial", Lancel Oncol., Aug. 2012, vol. 13, pp. 773-781.
Johannessen et al., "COT drives resistance to RAF inhibition through MAP kinase pathway reactivation" Nature 468:968-72 (2010).
Kefford et al., "Phase I/II study of GSK2118436, a selective inhibitor of oncogenic mutant BRAF kinase, in patients with metastatic melanoma and other solid tumors" J Clin Oncol (2010) ASCO meeting (suppl 15; abstr 8503).
Larkin et al., "Combined Vemurafenib and Cobimetinib in BRAF-Mutated Melanoma" The New England Journal of Medicine, Nov. 13, 2014, vol. 371, No. 20, pp. 1867-1876.
Moritz et al., "Akt-RSK-S6 kinase signaling networks activated by oncogenic receptor tyrosine kinases" Sci Signal. 3(136):ra64 (2010).
Musib et al., "Abstract 1304: Clinical pharmacokinetics of GDC-0973, an oral MEK inhibitor, in cancer patients: data from a Phase 1 study", Proceedings: AACR 102nd Annual Meeting, Apr. 2011, 4 pages.
Nazarian et al., "Melanomas acquire resistance to B-RAF(V600E) inhibition by RTK or N-RAS upregulation" Nature 468:973-7 (2010).
Rahman, A., "Vemurafenib and cobimetinib in BRAF-mutated melanoma" Oncology, Nov. 2014, vol. 15, pp. e535.
Ribas et al., "Combination of vemurafenib and cobimetinib in patients with advanced BRAFV(600)-mutated melanoma: a phase Ib study" Lancet Oncol, Aug. 2014, vol. 15, pp. 954-965.
Ribas, Antoni, "Combination Therapies Building on the Efficacy of CTLA4 and BRAF Inhibitors for Metastatic Melanoma", American Society of Clinical Oncology, 2012 Educational Book, 48th Annual Meeting, Jun. 2012, pp. 675-678.
Rosen et al., "Abstract 4716: A first-in-human phase 1 study to evaluate the MEK1/2 inhibitor GDC-0973 administered daily in patients with advanced solid tumors", Proceedings: AACR 102nd Annual Meeting, Apr. 2011, 5 pages.
Sharfman, William H., "Encorafenib and Binimetinib: A New Benchmark in Metastatic Melanoma Therapy?", The ASCO Post, Dec. 10, 2018, 5 pages.
Sharma et al., "Oncogene addiction: setting the stage for molecularly targeted cancer therapy" Genes Dev. 21(24):3214-31 (2007).
Sharma et al., "Targeting mitogen-activated protein kinase/extracellular signal-regulated kinase kinase in the mutant (V600E) B-Raf signaling cascade effectively inhibits melanoma lung metastases" Cancer Res. 66(16):8200—(2006).

(56) References Cited

OTHER PUBLICATIONS

Sosman et al., "Survival in BRAF V600-mutant advanced melanoma treated with vemurafenib" N Engl J Med. 366(8):707-14 (2012).
Su et al., "RAS mutations in cutaneous squamous-cell carcinomas in patients treated with BRAF inhibitors" N Engl J Med. 366(3):207-15 (2012).
Takezawa et al., "Sorafenib inhibits non-small cell lung cancer cell growth by targeting B-RAF in KRAS wild-type cells and C-RAF in KRAS mutant cells" Cancer Res. 69(16):6515-21 (2009).
Vergani et al., "Identification of MET and SRC activation in melanoma cell lines showing primary resistance to PLX4032" Neoplasia 13(12):1132-42 (2011).
Wan et al., "Mechanism of activation of the RAF-ERK signaling pathway by oncogenic mutations of B-RAF" Cell 116(6):855-67 (2004).
Weber et al., "Updated safety and efficacy results from a phase I/II study of the oral BRAF inhibitor dabrafenib (GSK2118436) combined with the oral MEK 1/2 inhibitor trannetinib (GSK1120212) inpatients with BRAFi-naive metastatic melanoma", J. Clin. Oncol., May 2012, vol. 30, No. 15 suppl, p. 8510.
Wilhelm et al., "BAY 43-9006 Exhibits Broad Spectrum Oral Antitumor Activity and Targets the RAF/MEK/ERK Pathway and Receptor Tyronise Kinases Involved in Tumor Progression and Angiogenesis" Cancer Research 64:7099-7109 (Oct. 2004).
Wong et al., "Bridging the Gap between Preclinical and Clinical Studies Using Pharmacokinetic-Pharmacodynamic Modeling: An Analysis of GDC-0973, a MEK Inhibitor", Clinical Cancer Research, 2012, pp. 3090-3099.
Zelboraf Label, Highlights of Prescribing Information, Aug. 2011, 21 pages.
PCT ISR for PCT/EP2013/067050.

* cited by examiner

| Treated patients (n=70) | |
|---|---|
| Median age, years (range) | 57.5 years (19–76) |
| Gender, n (%)<br>Male<br>Female | <br>49 (70.0)<br>21 (30.0) |
| ECOG performance status, n (%)<br>PS 0<br>PS 1 | <br>35 (50.0)<br>35 (50.0) |
| LDH at screening or on Cycle 1 Day 1, n (%)<br>Elevated | <br>44 (63.0) |
| Melanoma stage at enrollment, n (%)<br>Unresectable stage IIIc<br>Stage IV, M1a<br>Stage IV, M1b<br>Stage IV, M1c | <br>6 (8.6)<br>2 (2.9)<br>10 (14.3)<br>52 (74.3) |
| Vemurafenib progressors, n (%) | 38 (54.3) |
| Median treatment cycles | 3 cycles (1 – 13) |

*FIG. 3*

| All pts (n=70) | Vemurafenib | GDC-0973 | Vem and GDC-0973 |
|---|---|---|---|
| Temporary interruption | 17 (24.3%) | 15 (21.4%) | 13 (8.6%) |
| Dose reduction | 3 (4.3%) | 2 (2.9%) | 2 (2.9%) |
| Permanent discontinuation due to AE | 1 (1.4%) | 0 (0%) | 0 (0%) |

*FIG. 5*

| Most common AEs attributed to either vemurafenib or GDC-0973 | | | | |
|---|---|---|---|---|
| n=70 | Grade 3 or 4 | | Total | |
| | n | % | n | % |
| Total number of patients with AEs | 20 | 28.6 | 67 | 95.7 |
| Non-acneiform rash[a] | 5 | 7.1 | 37 | 52.9 |
| Diarrhea | 4 | 5.7 | 36 | 51.4 |
| Photosensitivity / Sunburn | 0 | 0 | 22 | 31.4 |
| Fatigue | 1 | 1.4 | 21 | 30.0 |
| Nausea | 1 | 1.4 | 20 | 28.6 |
| Selected AEs attributed to either vemurafenib or GDC-0973 | | | | |
| Creatine phosphokinase elevation | 3 | 4.3 | 14 | 20.0 |
| Liver function test elevation[b] | 3 | 4.3 | 14 | 20.0 |
| Arthralgia | 1 | 1.4 | 9 | 12.9 |
| Serous choreoretinopathy[c] | 0 | 0 | 3 | 4.3 |
| Cutaneous squamous cell carcinoma, KA | 1 | 1.4 | 1 | 1.4 |

*Includes all patients reporting each of AE general terms, even for zero incidence.
[a]Non-acneiform rash includes MedDRA terms rash, rash generalised, rash maculo-papular, rash macular, rash papular, rash erythematous, erythema, rash pruritic, dermatitis, skin exfoliation, dermatitis exfoliative, lividity
[b]LFT elevation includes MedDRA terms alkaline phosphatase increased, bilirubin increased, hyperbilirubinaemia, AST & ALT increased, transaminases increased, and gamma-glutamyltransferase increased.
[c]Serous choreoretinopathy includes MedDRA terms chorioretinal disorder, chorioretinopathy, 1 pt with blurred vision later diagnosed as serous choreoretinopathy.

FIG. 4

Examples of PET Responses on Vemurafenib (Vem) + GDC-0973 (GDC) in Patients Who Progressed on Vemurafenib Examples of PET Responses on Vemurafenib (Vem) + GDC-0973 (GDC) in Patients Who Progressed on Vemurafenib

COMBINATION THERAPIES

CROSS-REFERENCE TO RELATED APPLICATIONS

This application is a continuation of U.S. patent application Ser. No. 13/967,782, filed Aug. 15, 2013, which claims priority to U.S. patent application No. 61/684,673 filed Aug. 17, 2012, U.S. patent application No. 61/705,575, filed Sep. 25, 2012, U.S. patent application No. 61/706,026, filed Sep. 26, 2012, U.S. patent application No. 61/722,725, filed Nov. 5, 2012, and U.S. patent application No. 61/780,708, filed Mar. 13, 2013, which are incorporated by reference in their entirety.

FIELD OF THE INVENTION

The present invention relates generally to the fields of molecular biology and signal transduction. More specifically, the invention relates to therapies for the treatment of pathological conditions, such as cancer.

BACKGROUND

Cancer remains to be one of the most deadly threats to human health. Worldwide, the number of melanoma cases is increasing at a rate that is faster than that of any other human cancer (Roberts et al., Br. J. Dermatol (2002) 146:7-17, Boyle et al., Ann oncol (2004) 15:5-6). While annual incidence rates vary across populations, in general, the rise in incidence has been greater in fair-skinned Caucasian populations (approximately 3-7% per year). Each year, it is estimated that approximately 132,000 new cases of melanoma will develop worldwide and about 37,000 deaths from melanoma will occur. In the US, there were 68,720 new cases and 8,650 deaths from melanoma in 2009 (Jemal et al., CA Cancer J Clin (2009) 59:225-49). The clinical outcome of patients with melanoma is highly dependent on the stage at presentation. Metastatic melanoma is one of the most deadly cancers. Despite recent success in the development of new therapies for melanoma, the vast majority of patients eventually succumb to their disease; hence, there remains a significant unmet need for improvement of outcomes in this segment of the melanoma patient population.

Vemurafenib is FDA-approved for treatment of patients with unresectable or metastatic melanoma that is BRAFV600E mutation-positive using the Cobas® 4800 BRAF V600 Mutation Test (see ZELBORAF® [vemurafenib] package insert). Vemurafenib was associated with a 63% reduction in the risk of death and a 74% decrease in the risk of disease progression or death, when compared with dacarbazine (Chapman et al., NEJM (2011) 364 (26):2507-16. Moreover, vemurafenib treatment led to response rates consistently greater than 50% and median OS of 14 to 16 months (Flaherty et al., NEJM (2010) 363:809-819; Chapman et al., id.; Sosman et al., NEJM (2012) 366(8):707).

SUMMARY OF THE INVENTION

The present invention provides combination therapies for treating a pathological condition, such as cancer, wherein a MEK inhibitor is combined with a BRAF inhibitor, thereby providing significant anti-tumor activity. In particular, the invention provides data from a clinical trial of BRAF inhibitor in combination with MEK inhibitor in patients having $BRAF^{V600}$ mutation-positive unresectable or metastatic melanoma.

In one aspect, provided are methods of treating (e.g., therapeutically treating) a patient (interchangeably termed "individual" herein) having $BRAF^{V600}$ mutation-positive cancer comprising administering to the patient (i) a first composition comprising [3,4-difluoro-2-[(2-fluoro-4-iodophenyl)amino]phenyl][3-hydroxy-3-[(2S)-2-piperidinyl]-1-azetidinyl]methanone (Compound II), or a pharmaceutically acceptable salt thereof; and (ii) a second composition comprising propane-1-sulfonic acid {3-[5-(4-chlorophenyl)-1H-pyrrolo[2,3-b]pyridine-3-carbonyl]-2,4-difluoro-phenyl}-amide (Compound I), or a pharmaceutically acceptable salt thereof, at a dose of 960 mg twice daily, on days 1-28 of a 28 day cycle.

In one aspect, provided are methods of treating (e.g., therapeutically treating) a patient having $BRAF^{V600}$ mutation-positive unresectable or metastatic melanoma comprising administering to the patient (i) a first composition comprising compound II, or a pharmaceutically acceptable salt thereof, at a dose of 60 mg (e.g., one 60 mg tablet), on days 1-21 of a 28 day cycle; and (ii) a second composition comprising compound I, or a pharmaceutically acceptable salt thereof, at a dose of 960 mg (e.g., four 240 mg tablets) twice daily, on days 1-28 of the 28 day cycle.

In some embodiments, Compound I, or a pharmaceutically-acceptable salt thereof, is substantially in amorphous form. In some embodiments, Compound I, or a pharmaceutically-acceptable salt thereof, is in amorphous form. In some embodiments, Compound I, or a pharmaceutically-acceptable salt thereof, is contained in a solid molecular complex formed with hydroxypropyl methyl cellulose acetate succinate such that it is immobilized in its amorphous form. In some embodiments, the amounts of Compound I, or a pharmaceutically-acceptable salt thereof, and hydroxypropyl methyl cellulose acetate succinate (HPMC-AS) in said complex are in a ratio of from about 1:9 to about 5:5, respectively. In some embodiments, the amounts of Compound I, or a pharmaceutically-acceptable salt thereof, and hydroxypropyl methyl cellulose acetate succinate in said complex are in a ratio of from about 2:8 to about 4:6, respectively. In some embodiments, the amounts of Compound I, or a pharmaceutically-acceptable salt thereof, and hydroxypropyl methyl cellulose acetate succinate in said complex are in a ratio of about 3:7, respectively. In some embodiments, the second composition comprises a blend wherein about 97% by weight of the blend is the aforementioned solid molecular complex and about 3% by weight of the blend is silicon dioxide. In some embodiments, the second composition comprises a suspension of the aforementioned solid molecular complex in a pharmaceutically acceptable carrier. In some embodiments, the second composition comprises a tablet comprising a solid molecular complex of Compound I, or a pharmaceutically-acceptable salt thereof, and HPMC-AS. In some embodiments, Compound I is provided as a tablet. In some embodiments, Compound I is provided as a 240 mg tablet (i.e., a tablet comprising 240 mg of Compound I). In some embodiments, compound I is provided as a tablet marketed as ZELBORAF®.

In some embodiments, the first composition comprising Compound II comprises one or more of lactose monohydrate, microcrystalline cellulose, croscarmellose sodium, and magnesium stearate. In some embodiments, Compound II is provided as a tablet comprising lactose monohydrate, microcrystalline cellulose, croscarmellose sodium, and magnesium stearate. In some embodiments, the tablet comprises a tablet coating comprising polyvinyl alcohol-part hydrolyzed, titanium dioxide, polyethylene glycol 3350, and talc.

In some embodiments, Compound II is provided as a 20 mg tablet, as a 40 mg tablet, or as a 60 mg tablet (i.e., a tablet comprising 60 mg of Compound II). In some embodiments, Compound II is provided as a 60 mg tablet. In some embodiments, the 60 mg tablet is provided in a pill card or blister pack.

In some embodiments, dosing may be concurrent or sequential, and administration may be as a combined formulation or as separate formulations. In some embodiments, the first composition (comprising Compound II) is administered sequentially with the second composition (comprising Compound I) (including but not limited to: one of more tablets comprising Compound I are administered, then one or more tablets of Compound II; one or more Compound I tablets are administered, then one or more Compound II tablets, then one or more Compound I tablets). In some embodiments, the first composition is administered prior to the second composition. In some embodiments, the second composition is administered prior to the first composition. In some embodiments, the first composition is administered concurrently with the second composition. In some embodiments, the first composition is administered concurrently with the second composition, followed by administration of the first compound. In some embodiments, the first and second compositions are provided as a combined preparation (in some embodiments, as a tablet). In some embodiments, the first and second compositions are co-formulated (e.g., as a pharmaceutical formulation). In some embodiments, a second 960 mg dose (e.g., four 240 mg tablets) of Compound I, or a pharmaceutically acceptable salt thereof is administered about 12 hours after a first 960 mg (e.g., four 240 mg tablets) dose of Compound I, or a pharmaceutically acceptable salt thereof. In some embodiments, Compound I, or a pharmaceutically acceptable salt thereof, and Compound II, or a pharmaceutically acceptable salt thereof, are each administered orally, with or without food. In some embodiments, Compound I, or a pharmaceutically acceptable salt thereof, and Compound II, or a pharmaceutically acceptable salt thereof, are each administered orally, with food. In some embodiments, Compound I, or a pharmaceutically acceptable salt thereof, and Compound II, or a pharmaceutically acceptable salt thereof, are each administered orally, without food.

In some embodiments, the unresectable or metastatic melanoma is BRAF$^{V600E}$ mutation-positive melanoma. In some embodiments, the unresectable or metastatic melanoma is metastatic melanoma. In some embodiments, the unresectable or metastatic melanoma is unresectable melanoma. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

In some embodiments, BRAF$^{V600}$ mutation is determined using a method comprising (a) performing PCR or sequencing on nucleic acid (e.g., DNA, e.g., genomic DNA) extracted from a sample of the patient's melanoma; and (b) determining expression of BRAF$^{V600}$ in the sample. In some embodiments, the melanoma sample is formalin-fixed paraffin-embedded. In some embodiments, BRAF$^{V600}$ mutation is determined using a method comprising (a) isolating DNA (e.g., genomic DNA) from a sample of the patient's melanoma; (b) performing PCR or sequencing on nucleic acid (e.g., DNA) extracted from a sample of the patient's melanoma; and (c) determining expression of BRAF$^{V600}$ in the sample. In some embodiments, the melanoma sample is formalin-fixed paraffin-embedded.

In another aspect, provided are methods of extending duration of response to treatment (e.g., therapeutic treatment) in a patient having unresectable or metastatic melanoma (e.g., BRAF$^{V600}$ mutation-positive unresectable or metastatic melanoma) comprising administering to the patient (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, each day of the 28 day cycle.

In another aspect, provided are methods of delaying or preventing development of resistance to treatment (e.g., resistance to BRAF inhibitor treatment) in a patient having unresectable or metastatic melanoma (e.g., BRAF$^{V600}$ mutation-positive unresectable or metastatic melanoma) comprising administering to the patient (i) Compound II, or a pharmaceutically acceptable salt thereof, at a dose of 60 mg, on days 1-21 of a 28 day cycle; and (ii) Compound I, or a pharmaceutically acceptable salt thereof, at a dose of 960 mg twice daily, each day of the 28 day cycle.

In another aspect, provided are pharmaceutical products comprising (i) a first composition comprising [3,4-difluoro-2-[(2-fluoro-4-iodophenyl)amino]phenyl][3-hydroxy-3-[(2S)-2-piperidinyl]-1-azetidinyl]methanone (Compound II), or a pharmaceutically acceptable salt thereof; and (ii) a second composition comprising propane-1-sulfonic acid {3-[5-(4-chlorophenyl)-1H-pyrrolo[2,3-b]pyridine-3-carbonyl]-2,4-difluoro-phenyl}-amide (Compound I), or a pharmaceutically acceptable salt thereof; as a combined preparation for concurrent or sequential use in the treatment of BRAF$^{V600}$ mutation-positive unresectable or metastatic melanoma, wherein the Compound II is administered at a dose of 60 mg, on days 1-21 of a 28 day cycle, and wherein Compound I is administered at a dose of 960 mg, twice daily each day of the 28 day cycle.

In some embodiments, Compound I, or a pharmaceutically-acceptable salt thereof, is substantially in amorphous form. In some embodiments, Compound I, or a pharmaceutically-acceptable salt thereof, is in amorphous form. In some embodiments, Compound I, or a pharmaceutically-acceptable salt thereof, is contained in a solid molecular complex formed with hydroxypropyl methyl cellulose acetate succinate such that it is immobilized in its amorphous form. In some embodiments, the amounts of Compound I, or a pharmaceutically-acceptable salt thereof, and hydroxypropyl methyl cellulose acetate succinate in said complex are in a ratio of from about 1:9 to about 5:5, respectively. In some embodiments, the amounts of Compound I, or a pharmaceutically-acceptable salt thereof, and hydroxypropyl methyl cellulose acetate succinate in said complex are in a ratio of from about 2:8 to about 4:6, respectively. In some embodiments, the amounts of Compound I, or a pharmaceutically-acceptable salt thereof, and hydroxypropyl methyl cellulose acetate succinate in said complex are in a ratio of about 3:7, respectively. In some embodiments, the second composition comprises a blend wherein about 97% by weight of the blend is the aforementioned solid molecular complex and about 3% by weight of the blend is silicon dioxide. In some embodiments, the second composition comprises a suspension of the aforementioned solid molecular complex in a pharmaceutically acceptable carrier. In some embodiments, the second composition comprises a tablet comprising a solid molecular complex of Compound I, or a pharmaceutically-acceptable salt thereof, and HPMC-AS. In some embodiments, Compound I is provided as a tablet. In some embodiments, Compound I is provided as a 240 mg tablet (i.e., a tablet comprising 240 mg of Compound I).

In some embodiments, the first composition comprises one or more of lactose monohydrate, microcrystalline cellulose, croscarmellose sodium, and magnesium stearate. In some embodiments, Compound II is provided as a tablet comprising lactose monohydrate, microcrystalline cellulose, croscarmellose sodium, and magnesium stearate. In some embodiments, the tablet comprises a tablet coating comprising polyvinyl alcohol-part hydrolyzed, titanium dioxide, polyethylene glycol 3350, and talc. In some embodiments, Compound II is provided as a 20 mg tablet, as a 40 mg tablet, or as a 60 mg tablet. In some embodiments, Compound II is provided as a 60 mg tablet. In some embodiments, compound I is provided as a tablet marketed as ZELBORAF®.

In some embodiments, dosing may be concurrent or sequential, and administration may be as a combined formulation or as separate formulations. In some embodiments, the first composition (comprising Compound II) is administered sequentially with the second composition (comprising Compound I) (including but not limited to: one of more tablets comprising Compound I are administered, then one or more tablets of Compound II; one or more Compound I tablets are administered, then one or more Compound II tablets, then one or more Compound I tablets). In some embodiments, the first composition is administered prior to the second composition. In some embodiments, the second composition is administered prior to the first composition. In some embodiments, the first composition is administered concurrently with the second composition. In some embodiments, the first composition is administered concurrently with the second composition, followed by administration of the first compound. In some embodiments, the first and second compositions are provided as a combined preparation (in some embodiments, as a tablet). In some embodiments, the first and second compositions are co-formulated (e.g., as a pharmaceutical formulation). In some embodiments, a second 960 mg dose (e.g., four 240 mg tablets) of Compound I, or a pharmaceutically acceptable salt thereof is administered about 12 hours after a first 960 mg (e.g., four 240 mg tablets) dose of Compound I, or a pharmaceutically acceptable salt thereof. In some embodiments, Compound I, or a pharmaceutically acceptable salt thereof, and Compound II, or a pharmaceutically acceptable salt thereof, are each administered orally, with or without food. In some embodiments, Compound I, or a pharmaceutically acceptable salt thereof, and Compound II, or a pharmaceutically acceptable salt thereof, are each administered orally, with food. In some embodiments, Compound I, or a pharmaceutically acceptable salt thereof, and Compound II, or a pharmaceutically acceptable salt thereof, are each administered orally, without food.

In some embodiments, the unresectable or metastatic melanoma is BRAF$^{V600E}$ mutation-positive melanoma. In some embodiments, the unresectable or metastatic melanoma is metastatic melanoma. In some embodiments, the unresectable or metastatic melanoma is unresectable melanoma. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

In some embodiments, BRAF$^{V600}$ mutation is determined using a method comprising (a) performing PCR or sequencing on nucleic acid (e.g., DNA) extracted from a sample of the patient's melanoma; and (b) determining expression of BRAF$^{V600}$ in the sample. In some embodiments, the melanoma sample is a formalin-fixed paraffin-embedded sample.

In another aspect, provided are methods for selecting a therapy for a patient with unresectable or metastatic melanoma comprising determining presence of BRAF$^{V600}$ mutation in the patient's unresectable or metastatic melanoma sample, and selecting a cancer medicament based on the presence of BRAF$^{V600}$ mutation. In some embodiments, sample is shown to express BRAF$^{V600}$ mutation, and treatment with a composition comprising Compound II in combination with a composition comprising Compound I is selected. In some embodiments, the patient is treated for unresectable or metastatic melanoma with a method comprising administering to the patient (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, on days 1-28 of the 28 day cycle.

In another aspect, provided are methods for optimizing therapeutic efficacy comprising determining presence of BRAF$^{V600}$ mutation in a patient's unresectable or metastatic melanoma sample, and selecting a cancer medicament based on the presence of BRAF$^{V600}$ mutation. In some embodiments, the sample is shown to express BRAF$^{V600}$ mutation, and treatment with a first composition comprising Compound II in combination with a second composition comprising Compound I is selected. In some embodiments, the patient is treated for unresectable or metastatic melanoma with a method comprising administering to the patient (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, on days 1-28 of the 28 day cycle.

In some embodiments of any of the inventions described herein, presence (in some embodiments, presence or absence) of BRAF$^{V600}$ mutation is determined by assessing BRAF nucleic acid. In some embodiments, presence of BRAF$^{V600}$ mutation is determined using a method selected from: polymerase chain reaction (PCR) (including but not limited to quantitative real time PCR and allele-specific PCR), sequencing (including but not limited to Sanger sequencing and/or pyrosequencing), hybridization using allele-specific oligonucleotides, primer extension, allele-specific ligation, or electrophoretic separation techniques (including but not limited to singled-stranded conformational polymorphism (SSCP) and heteroduplex analysis), and 5' nuclease assays. In some embodiments, presence of BRAF$^{V600}$ mutation is determined using PCR or sequencing. In some embodiments, presence of BRAF$^{V600}$ mutation is determined by a method comprising (a) performing PCR on genomic DNA extracted from a sample of the patient's melanoma; and (b) determining expression of mutant BRAF polynucleotide by sequencing the PCR amplified nucleic acid. In some embodiments, presence of BRAF$^{V600}$ mutation is determined by a method (a) hybridizing a first and second oligonucleotides to at least one variant of the BRAF target sequence; wherein said first oligonucleotide is at least partially complementary to one or more variants of the target sequence and said second oligonucleotide is at least partially complementary to one or more variants of the target sequence, and has at least one internal selective nucleotide complementary to only one variant of the target sequence;

(b) extending the second oligonucleotide with a nucleic acid polymerase; wherein said polymerase is capable of extending said second oligonucleotide preferentially when said selective nucleotide forms a base pair with the target, and substantially less when said selective nucleotide does not form a base pair with the target; and (c) detecting the products of said oligonucleotide extension, wherein the extension signifies the presence of the variant of a target sequence to which the oligonucleotide has a complementary selective nucleotide. In some embodiments, the sample (melanoma sample) is a formalin-fixed paraffin-embedded sample. The sample may be obtained prior to the patient's treatment with a cancer medicament. The sample may be obtained from the primary tumor or from a metastatic tumor. The sample may be obtained when the cancer is first diagnosed and/or, for example, after the tumor has metastasized. In some embodiments, the metastasized tumor sample is of lung, skin, lymph node, bone, liver, colon, thyroid, and/or ovary.

In another aspect, the methods described herein further comprise treatment with an additional therapeutic agent. In some embodiments, the additional therapeutic agent is a cancer medicament.

In another aspect, provided are kits comprising (i) a first composition comprising Compound II, or a pharmaceutically acceptable salt thereof; and (ii) a second composition comprising Compound I, or a pharmaceutically acceptable salt thereof. In some embodiments, the kit comprises instructions for performing any of the methods described herein. In some embodiments, the instructions are for methods of treating (e.g., therapeutically treating) a patient having $BRAF^{V600}$ mutation-positive unresectable or metastatic melanoma comprising administering to the patient (i) a first composition comprising compound II, or a pharmaceutically acceptable salt thereof, at a dose of 60 mg, on days 1-21 of a 28 day cycle; and (ii) a second composition comprising compound I, or a pharmaceutically acceptable salt thereof, at a dose of 960 mg twice daily, on days 1-28 of the 28 day cycle. In some embodiments, the kits are for use in the treatment of $BRAF^{V600}$ mutation-positive unresectable or metastatic melanoma. In some embodiments, the melanoma is $BRAF^{V600E}$ mutation-positive unresectable or metastatic melanoma. In some embodiments, the unresectable or metastatic melanoma has not been previously treated. In some embodiments, the patient's unresectable or metastatic melanoma has been previously treated (in some embodiments, without prior treatment to BRAF inhibitor). In some embodiments, the first composition comprising Compound II is a tablet. In some embodiments, the second composition comprising Compound I is a tablet. In some embodiments, the first composition comprising Compound II and the first composition comprising Compound I are each provided as a tablet. In some embodiments, the first composition comprising Compound I and the second Composition comprising Compound II are provided as a single dosing form. In some embodiments, the first composition comprising Compound II and the second composition comprising Compound I are co-formulated (e.g., as a pharmaceutical formulation).

In another aspect, provided are articles of manufacture for use in treating (e.g., therapeutically treating) cancer (such as $BRAF^{V600}$-positive unresectable or metastatic melanoma) are provided. The article of manufacture comprises a container and a label or package insert on or associated with the container. Suitable containers include, for example, bottles, vials, syringes, pill packs, blister packs, dial packs, etc. In some embodiments, the article of manufacture comprises a container and a tablet comprising 60 mg of Compound II. In some embodiments, the article of manufacture comprises a container and a tablet comprising 20 mg or 40 mg of Compound II. In some embodiments, article of manufacture comprises a container comprising (a) a first composition comprising Compound II (e.g., 60 mg of Compound II) provided as a tablet and (b) a second composition comprising Compound I (e.g., 960 mg of Compound I) provided as a tablet. In some embodiments, the container is a pill pack or a blister pack. In some embodiments, the article of manufacture (e.g., provided as a pill pack or a blister pack) comprises 21 tablets of a composition comprising Compound II (e.g., 60 mg of Compound II); and tablets of a composition comprising Compound I (e.g., 960 mg of Compound I (e.g., four 240 mg tablets)). In some embodiments, the label provides instructions for any of the methods of treatment described herein.

In another aspect, provided are diagnostic kits useful for detecting any one or more of the biomarker(s) identified herein. Accordingly, a diagnostic kit is provided which comprises one or more reagents for determining expression of BRAF expression, such as expression of $BRAF^{V600}$ biomarker in a sample from a cancer patient. Optionally, the kit further comprises instructions to use the kit if the patient's unresectable or metastatic melanoma expresses $BRAF^{V600}$, to select Compound II in combination with Compound I for treating (e.g., therapeutically treating) the patient, wherein treatment comprises administering (i) Compound II, or a pharmaceutically acceptable salt thereof, at a dose of 60 mg, on days 1-21 of a 28 day cycle; and (ii) Compound I, or a pharmaceutically acceptable salt thereof, at a dose of 960 mg twice daily, on days 1-28 of the 28 day cycle. In some embodiments, the patient's unresectable or metastatic melanoma has not been previously treated. In some embodiments, the patient's unresectable or metastatic melanoma has been previously treated (in some embodiments, without prior treatment to BRAF inhibitor).

In another aspect, the invention provides methods for promoting or advertising a cancer medicament comprising promoting, to a target audience, the use of Compound II for treating (e.g., therapeutically treating) a patient with $BRAF^{V600}$ mutation-positive unresectable or metastatic melanoma, in combination with vemurafenib, wherein treatment comprises administering (i) Compound II, or a pharmaceutically acceptable salt thereof, at a dose of 60 mg, on days 1-21 of a 28 day cycle; and (ii) Compound I, or a pharmaceutically acceptable salt thereof, at a dose of 960 mg twice daily, on days 1-28 of the 28 day cycle. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

In another aspect, provided are business methods comprising marketing the use of Compound II for treating (e.g., therapeutically treating) a patient with $BRAF^{V600}$ mutation-positive unresectable or metastatic melanoma, in combination with Compound I, wherein treatment comprises administering (i) Compound II, or a pharmaceutically acceptable salt thereof, at a dose of 60 mg, on days 1-21 of a 28 day cycle; and (ii) Compound I, or a pharmaceutically acceptable salt thereof, at a dose of 960 mg twice daily, on days 1-28 of the 28 day cycle. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE FIGURES

FIG. 3: shows patient characteristics.

FIG. 4: shows adverse event attributed to either vemurafenib or GDC-0973 in all patients.

FIG. 5: shows adverse events that led to dose interruptions, reductions and permanent discontinuations.

DETAILED DESCRIPTION OF EMBODIMENTS OF THE INVENTION

I. Definitions

Figure 1:
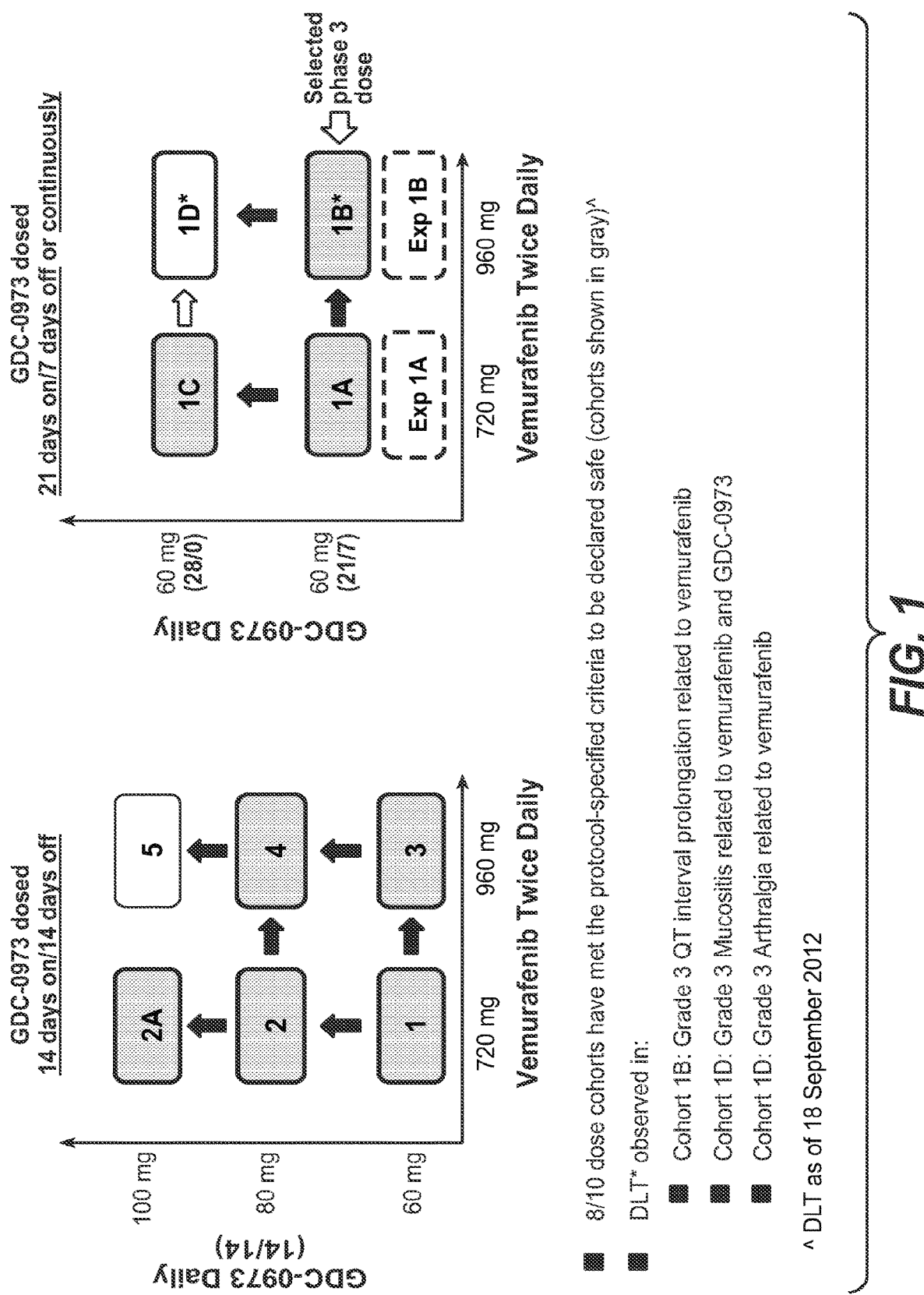
FIG. 1: shows a dose-escalation plan for the Phase Ib clinical trial comprising treatment with a combination of vemurafenib and GDC-0973, administered one of the following 28-day schedules: 14 consecutive days of study drug followed by a 14-day drug holiday (14/14), 21 consecutive days of study drug followed by a 7-day drug holiday (21/7), or as a continuous daily dose (28/0). Each treatment cycle was 28 days.

Herein, a "patient" (interchangeably termed "individual") is a human patient. The patient may be a "cancer patient", i.e. one who is suffering or at risk for suffering from one or more symptoms of cancer. The patient may be a "melanoma patient", i.e. one who is suffering or at risk for suffering from one or more symptoms of melanoma. In some embodiments, the patient may be an "unresectable or metastatic melanoma patient", i.e. one who is suffering or at risk for suffering from one or more symptoms of unresectable or metastatic melanoma.

The term "BRAF", as used herein, refers, unless indicated otherwise, to any native or variant (whether native or synthetic) BRAF polypeptide. The term "wild type BRAF" generally refers to a polypeptide comprising the amino acid sequence of a naturally occurring BRAF protein.

The term "BRAF variant" as used herein refers to a BRAF polypeptide which includes one or more amino acid mutations in the native BRAF sequence. Optionally, the one or more amino acid mutations include amino acid substitution(s).

As used herein, "BRAF$^{V600}$ mutation-positive melanoma" refers to a patient's melanoma (e.g., unresectable or metastatic melanoma) that has been shown to express BRAF$^{V600}$.

As used herein, "BRAF$^{V600E}$ mutation-positive melanoma" refers to a patient's melanoma (e.g., unresectable or metastatic melanoma) that has been shown to express BRAF$^{V600E}$.

The "V600" mutation of BRAF as used herein (interchangeably termed "BRAF$^{V600}$"), refers to a mutation in the BRAF protein wherein the valine amino acid residue at residue position 600 of BRAF is replaced by another amino acid residue. "V600" is also known as "V599" under a previous numbering system (Kumar et al., Clin. Cancer Res. 9:3362-3368, 2003).

The "V600E" mutation of BRAF as used herein, refers to a mutation in the BRAF protein wherein the valine residue at residue position 600 of BRAF is replaced by glutamic acid. "V600E" is also known as "V599E" under a previous numbering system (Kumar et al., Clin. Cancer Res. 9:3362-3368, 2003).

The term "mutation", as used herein, means a difference in the amino acid or nucleic acid sequence of a particular protein or nucleic acid (gene, RNA) relative to the wild-type protein or nucleic acid, respectively. A mutated protein or nucleic acid can be expressed from or found on one allele (heterozygous) or both alleles (homozygous) of a gene, and may be somatic or germ line. In the instant invention, mutations are generally somatic. Mutations include sequence rearrangements such as insertions, deletions, and point mutations (including single nucleotide/amino acid polymorphisms).

To "inhibit" is to decrease or reduce an activity, function, and/or amount as compared to a reference.

Protein "expression" refers to conversion of the information encoded in a gene into messenger RNA (mRNA) and then to the protein.

Herein, a sample or cell that "expresses" a protein of interest (such as BRAF$^{V600}$, for example BRAF$^{V600E}$) is one in which nucleic acid (e.g., DNA or mRNA) encoding the protein, or the protein, including fragments thereof, is determined to be present in the sample or cell. A cancer (e.g., unresectable or metastatic melanoma) that "expresses" a protein of interest (such as BRAF$^{V600}$, for example BRAF$^{V600E}$) is one in which nucleic acid (e.g., DNA or mRNA) encoding the protein, or the protein, including fragments thereof, is determined to be present in the sample of the cancer (e.g., unresectable or metastatic melanoma).

A "population" of patients refers to a group of patients with cancer, such as in a clinical trial, or as seen by oncologists following FDA approval for a particular indication, such as unresectable or metastatic melanoma cancer therapy. In some embodiments, the indication is BRAF$^{V600}$ mutation-positive unresectable or metastatic melanoma.

For the methods of the invention, the term "instructing" a patient means providing directions for applicable therapy, medication, treatment, treatment regimens, and the like, by any means, but preferably in writing, such as in the form of package inserts or other written promotional material.

For the methods of the invention, the term "promoting" means offering, advertising, selling, or describing a particular drug, combination of drugs, or treatment modality, by any means, including writing, such as in the form of package inserts. Promoting herein refers to promotion of therapeutic agent(s), such as an MEK inhibitor and/or BRAF inhibitor, for an indication, such as treatment for BRAF$^{V600}$ mutation-positive unresectable or metastatic melanoma, where such promoting is authorized by the Food and Drug Administration (FDA) as having been demonstrated to be associated with statistically significant therapeutic efficacy and acceptable safety in a population of subjects The term "marketing" is used herein to describe the promotion, selling or distribution of a product (e.g., drug). Marketing specifically includes packaging, advertising, and any business activity with the purpose of commercializing a product.

For the purposes herein, a "previously treated" cancer patient has received prior cancer therapy. A "previously treated" unresectable or metastatic melanoma patient has received prior therapy for unresectable or metastatic melanoma.

A "cancer medicament" is a drug effective for treating cancer.

The term "biomarker" or "marker" as used herein refers generally to a molecule, including a gene, mRNA, protein, carbohydrate structure, or glycolipid, the expression of which in or on a tissue or cell or secreted can be detected by known methods (or methods disclosed herein) and is predictive or can be used to predict (or aid prediction) for a cell, tissue, or patient's responsiveness to treatment regimes.

By "patient sample" is meant a collection of similar cells obtained from a cancer patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In one embodiment the sample is of unresectable or metastatic melanoma.

An "effective response" of a patient or a patient's "responsiveness" to treatment with a medicament and similar wording refers to the clinical or therapeutic benefit imparted to a patient at risk for, or suffering from, cancer (e.g., $BRAF^{V600}$ mutation-positive unresectable or metastatic melanoma) upon administration of the cancer medicament. Such benefit includes any one or more of: extending survival (including overall survival and progression free survival); resulting in an objective response (including a complete response or a partial response); or improving signs or symptoms of cancer, etc.

"Survival" refers to the patient remaining alive, and includes overall survival as well as progression free survival.

"Overall survival" refers to the patient remaining alive for a defined period of time from the time of diagnosis or treatment.

"Progression free survival" refers to the patient remaining alive, without the cancer progressing or getting worse.

By "extending survival" is meant increasing overall or progression free survival in a treated patient relative to an untreated patient (i.e. relative to a patient not treated with the medicament), or relative to a patient who does not express a biomarker at the designated level, and/or relative to a patient treated with an approved cancer medicament, such as vemurafenib.

An "objective response" refers to a measurable response, including complete response (CR) or partial response (PR).

By "complete response" or "CR" is intended the disappearance of all signs of cancer in response to treatment. This does not always mean the cancer has been cured.

A "partial response" or "PR" refers to a decrease in the size of one or more tumors or lesions, or in the extent of cancer in the body, in response to treatment.

"Treatment" refers to both therapeutic treatment and prophylactic or preventative measures.

The term "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

The terms "cancer" and "cancerous" refer to or describe the physiological condition in mammals that is typically characterized by unregulated cell growth. Included in this definition are benign and malignant cancers. In some embodiments, the cancer is unresectable or metastatic melanoma that expresses or has been shown to express $BRAF^{V600}$.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

A "target audience" is a group of people or an institution to whom or to which a particular medicament is being promoted or intended to be promoted, as by marketing or advertising, especially for particular uses, treatments, or indications, such as patient patients, patient populations, readers of newspapers, medical literature, and magazines, television or internet viewers, radio or internet listeners, physicians, drug companies, etc.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

The term "pharmaceutical formulation" refers to a sterile preparation that is in such form as to permit the biological activity of the medicament to be effective, and which contains no additional components that are unacceptably toxic to a subject to which the formulation would be administered.

A "sterile" formulation is aseptic or free from all living microorganisms and their spores.

A "kit" is any manufacture (e.g. a package or container) comprising at least one reagent, e.g., a medicament for treatment of cancer (e.g., unresectable or metastatic melanoma), or a reagent (e.g., primer) for specifically detecting a biomarker gene or protein. The manufacture is preferably promoted, distributed, or sold as a unit for performing the methods of the present invention.

A "pharmaceutically acceptable carrier" refers to an ingredient in a pharmaceutical formulation, other than an active ingredient, which is nontoxic to a subject. A non-limiting list of exemplary pharmaceutically acceptable carriers is a buffer, excipient, stabilizer, or preservative.

The phrase "pharmaceutically acceptable salt" as used herein, refers to pharmaceutically acceptable organic or inorganic salts of a compound.

As used herein, the term "substantially amorphous" material means material which has no more than about 10% crystallinity; and "amorphous" material means material which has no more than about 2% crystallinity.

The term "molecularly dispersed", as used herein, refers to the random distribution of a compound (e.g., Compound I) with a polymer In certain embodiments the compound is present in the polymer in a final state of subdivision See, e.g., M G, Vachon et al., *J Microencapsulation*, 14 281-301 (1997) and Vandelli et al., *J Microencapsulation,* 10-55-65 (1993). In some embodiments, a compound (for example. Compound I) may be dispersed within a matrix formed by the polymer in its solid state such that the compound is immobilized m its amorphous form. Whether a compound is molecularly dispersed in a polymer may be evidenced in a variety of ways, e.g., by the resulting solid molecular complex having a single glass transition temperature.

The term "solid molecular complex" as used herein means a solid dispersion that includes Compound I molecularly dispersed within a polymer matrix.

The term "immobilize", as used herein with reference to the immobilization of the active compound in the polymer matrix, means that molecules of the compound interact with molecules of the polymer in such a way that the molecules of the compound are held in the aforementioned matrix and prevented from crystal nucleation due to lack of mobility In some embodiments the polymer may prevent intermolecular hydrogen bonding or weak dispersion forces between two or more drug molecules of Compound I. See, for example, Matsumoro and Zografi, *Pharmaceutical Research*, Vol. 16. No. 11, p 1722-1728, 1999.

II. Cancer Medicaments

In one aspect, the present invention features the use of MEK inhibitors and BRAF inhibitors in combination therapy to treat a pathological condition, such as cancer, in a patient. In another aspect, the invention concerns selecting patients who can be treated with MEK inhibitors and BRAF inhibitors based on expression of one or more of the biomarkers disclosed herein.

Vemurafenib

Vemurafenib is an orally available inhibitor of some mutated forms of BRAF serine/threonine kinase, including $BRAF^{V600E}$. Vemurafenib is available as 240 mg tablets for oral use. Vemurafenib, also termed "Compound I" herein, has the chemical name propane-1-sulfonic acid {3-[5-(4-chlorophenyl)-1H-pyrrolo[2,3-b]pyridine-3-carbonyl]-2,4-difluoro-phenyl}-amide. This compound is disclosed in WO 2007/002325 (see e.g., page 80 and corresponding formula on page 82). Compound I has the following chemical structure:

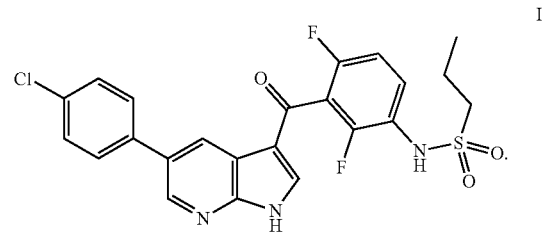 [SMILES: CCCS(=O)(=O)Nc1ccc(F)c(C(=O)c2c[nH]c3ncc(-c4ccc(Cl)cc4)cc23)c1F]

Compound I exists in its natural, i.e. thermodynamically stable, state in a crystalline form. However, the amorphous form of the compound has greater solubility in water as compared with the crystalline form and thus has an improved dissolution rate and, therefore, improved bioavailability as compared to the crystalline form. Accordingly, in some embodiments of the present invention, Compound I is in substantially amorphous form and, in some embodiments, in amorphous form.

GDC-0973

GDC-0973 (also termed "cobimetinib" or "Compound II" herein) is an orally available, potent and highly selective inhibitor of MEK1 and MEK2, central components of the RAS/RAF pathway. GDC-0973 has the chemical name [3,4-difluoro-2-[(2-fluoro-4-iodophenyl)amino]phenyl][3-hydroxy-3-[(2S)-2-piperidinyl]-1-azetidinyl]methanone. GDC-0973 has the chemical structure:

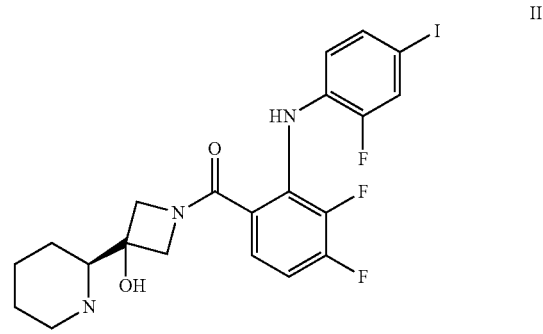 [SMILES: O=C(c1ccc(F)c(F)c1Nc1ccc(I)cc1F)N1CC(O)([C@@H]2CCCCN2)C1]

Compound II may be prepared following the methods described in US2009/0156576 (the contents of which are hereby incorporated by reference). Compound II has the following CAS Registry Number: 934660-93-2.

Additional Therapeutic Agents

The combination therapy of the invention can additionally comprise treatment with one or more therapeutic agent(s). In some embodiments, the one or more therapeutic agent is one or more cancer medicament(s). The combined administration includes concurrent administration, using separate formulations or a single pharmaceutical formulation, and sequential administration in either order, wherein preferably there is a time period while both (or all) active agents simultaneously exert their biological activities. The therapeutic agent, if administered, is usually administered at dosages known therefor, or optionally lowered due to combined action of the drugs. Preparation and dosing schedules for such therapeutic agents may be used according to manufacturers' instructions or as determined empirically by the skilled practitioner. In some embodiments, the additional therapeutic agent is a chemotherapeutic agent.

III. Combination Therapies

In one aspect, provided are methods for treating a patient having cancer comprising administering an effective (e.g., a therapeutically effective) amount of BRAF inhibitor (e.g., vemurafenib) and MEK inhibitor (e.g., GDC-0973). Methods include any treatment methods herein.

In one aspect, provided are methods of treating (e.g., therapeutically treating) a patient having BRAF$^{V600}$ mutation-positive cancer comprising administering to the patient (i) a first composition comprising [3,4-difluoro-2-[(2-fluoro-4-iodophenyl)amino]phenyl][3-hydroxy-3-[(2S)-2-piperidinyl]-1-azetidinyl]methanone (Compound II), or a pharmaceutically acceptable salt thereof; and (ii) a second composition comprising propane-1-sulfonic acid {3-[5-(4-chlorophenyl)-1H-pyrrolo[2,3-b]pyridine-3-carbonyl]-2,4-difluoro-phenyl}-amide (Compound I), or a pharmaceutically acceptable salt thereof, at a dose of 960 mg (e.g., four 240 mg tablets) twice daily, on days 1-28 of a 28 day cycle.

In one aspect, provided are methods of treating (e.g., therapeutically treating) a patient having BRAF$^{V600}$ mutation-positive unresectable or metastatic melanoma comprising administering to the patient (i) a first composition comprising compound II, or a pharmaceutically acceptable salt thereof, at a dose of 60 mg, on days 1-21 of a 28 day cycle; and (ii) a second composition comprising compound I, or a pharmaceutically acceptable salt thereof, at a dose of 960 mg twice daily, on days 1-28 of the 28 day cycle.

In one aspect, methods are provided for extending duration of response to treatment in a patient having unresectable or metastatic melanoma comprising administering to the patient (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, each day of the 28 day cycle. In some embodiments, duration of response to the combination treatment is extended relative to duration of response to Compound I treatment (e.g. Compound I monotherapy treatment).

In one aspect, methods are provided of delaying or preventing development of resistance to treatment (e.g., resistance to BRAF inhibitor treatment) in a patient having unresectable or metastatic melanoma comprising administering to the patient (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, each day of the 28 day cycle. In some embodiments, development of resistance to the combination treatment is delayed relative to development of resistance to Compound I treatment (e.g., Compound I monotherapy treatment).

In another aspect, a composition is provided for use in treating (e.g., therapeutically treating) a patient with unresectable or metastatic melanoma comprising a first composition comprising compound II, or a pharmaceutically acceptable salt thereof, wherein said use comprises simultaneous or sequential administration of a second composition comprising compound I; wherein the first composition comprising compound II is administered at a dose of 60 mg, on days 1-21 of a 28 day cycle, and wherein the second composition comprising compound I is administered at a dose of 960 mg, twice daily each day of the 28 day cycle.

In some embodiments of any of the methods of treatment herein, the patient has not received prior treatment for the unresectable or metastatic melanoma. In some embodiments, the patient's unresectable or metastatic melanoma has been previously treated (in some embodiments, without prior treatment to BRAF inhibitor). In some embodiments, the patient has not received prior treatment with a Raf pathway inhibitor. In some embodiments, the patient has not received prior treatment with a MEK pathway inhibitor. In some embodiments, the patient has not received prior treatment with a Raf pathway inhibitor or a MEK pathway inhibitor. In some embodiments, the patient has received prior adjuvant treatment. In some embodiments, the patient has not received prior treatment with a Raf pathway inhibitor and has received prior adjuvant treatment. In some embodiments, the patient has not received prior treatment with a MEK pathway inhibitor and has received prior adjuvant treatment. In some embodiments, the patient has not received prior treatment with a Raf pathway inhibitor or a MEK pathway inhibitor and has received prior adjuvant treatment.

Cancer staging systems describe how far the cancer has spread anatomically and attempt to put patients with similar prognosis and treatment in the same staging group. Several tests may be performed to help stage cancer including biopsy and certain imaging tests such as a chest x-ray, mammogram, bone scan, CT scan, and MRI scan. Blood tests and a clinical evaluation are also used to evaluate a patient's overall health and detect whether the cancer has spread to certain organs.

To stage cancer, the American Joint Committee on Cancer first places the cancer, particularly solid tumors, in a letter category using the TNM classification system. Cancers are designated the letter T (tumor size), N (palpable nodes), and/or M (metastases). T1, T2, T3, and T4 describe the increasing size of the primary lesion; N0, N1, N2, N3 indicates progressively advancing node involvement; and M0 and M1 reflect the absence or presence of distant metastases.

In the second staging method, also known as the Overall Stage Grouping or Roman Numeral Staging, cancers are divided into stages 0 to IV, incorporating the size of primary lesions as well as the presence of nodal spread and of distant metastases. In this system, cases are grouped into four stages denoted by Roman numerals I through IV, or are classified as "recurrent." For some cancers, stage 0 is referred to as "in situ" or "Tis," such as ductal carcinoma in situ or lobular carcinoma in situ for breast cancers. High grade adenomas can also be classified as stage 0. In general, stage I cancers are small localized cancers that are usually curable, while stage IV usually represents inoperable or metastatic cancer.

Stage II and III cancers are usually locally advanced and/or exhibit involvement of local lymph nodes. In general, the higher stage numbers indicate more extensive disease, including greater tumor size and/or spread of the cancer to nearby lymph nodes and/or organs adjacent to the primary tumor. These stages are defined precisely, but the definition is different for each kind of cancer and is known to the skilled artisan.

Many cancer registries, such as the NCI's Surveillance, Epidemiology, and End Results Program (SEER), use summary staging. This system is used for all types of cancer. It groups cancer cases into five main categories:

In situ is early cancer that is present only in the layer of cells in which it began.

Localized is cancer that is limited to the organ in which it began, without evidence of spread.

Regional is cancer that has spread beyond the original (primary) site to nearby lymph nodes or organs and tissues.

Distant is cancer that has spread from the primary site to distant organs or distant lymph nodes.

Unknown is used to describe cases for which there is not enough information to indicate a stage.

The American Joint Committee on Cancer (AJCC) TNM Staging for Melanoma is a system for staging melanoma. In some embodiments, the melanoma is unresectable stage IIIC. In some embodiments, the melanoma is stage M1a. In some embodiments, the melanoma is stage M1b. In some embodiments, the melanoma is stage M1c.

In addition, it is common for cancer to return months or years after the primary tumor has been removed. Cancer that recurs after all visible tumor has been eradicated, is called recurrent disease. Disease that recurs in the area of the primary tumor is locally recurrent, and disease that recurs as metastases is referred to as a distant recurrence.

In one aspect, the cancer patient is treated (e.g., therapeutically treated) with an additional cancer medicament. In some embodiments, the additional cancer medicament is a chemotherapeutic agent.

The therapeutic agents used in the invention will be formulated, dosed, and administered in a fashion consistent with good medical practice. Factors for consideration in this context include the particular disorder being treated, the particular patient being treated, the clinical condition of the patient, the cause of the disorder, the site of delivery of the agent, the method of administration, the scheduling of administration, the drug-drug interaction of the agents to be combined, and other factors known to medical practitioners.

Therapeutic formulations may be prepared using standard methods known in the art by mixing the active ingredient having the desired degree of purity with optional physiologically acceptable carriers, excipients or stabilizers (Remington's Pharmaceutical Sciences (20th edition), ed. A. Gennaro, 2000, Lippincott, Williams & Wilkins, Philadelphia, Pa.). Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The compositions may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound or pharmaceutical composition thereof) or aid in the manufacturing of the pharmaceutical product (i.e., medicament). In some embodiments, the compound is formulated together with a pharmaceutically acceptable carrier or excipient.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Pharmaceutically acceptable salts are described herein and known in the art. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion. If the compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18th ed., (1995) Mack Publishing Co., Easton Pa.; and in The Orange Book (Food & Drug Administration, Washington, D.C. on their website). If the compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium. Pharmaceutically acceptable salts, hydrates and other solid forms such as for example polymorphs of vemurafenib are disclosed in International Patent Application No. PCT/US2012/025965.

In some embodiments, Compound II is provided as a 20 mg tablet, as a 40 mg table, and/or as a 60 mg tablet. In some embodiments, Compound II is provided as a 60 mg tablet. In some embodiments, Compound II is provided as a tablet comprising one or more of lactose monohydrate, microcrystalline cellulose, croscarmellose sodium, and magnesium stearate for the tablet core. In some embodiments, the tablet coating comprises one or more of polyvinyl alcohol-part hydrolyzed, titanium dioxide, polyethylene glycol 3350, and talc. In some embodiments, Compound II is provided as a tablet comprising of lactose monohydrate, microcrystalline cellulose, croscarmellose sodium, and magnesium stearate for the tablet core, and a tablet coating comprising polyvinyl alcohol-part hydrolyzed, titanium dioxide, polyethylene glycol 3350, and talc. In some embodiments, Compound II is provided as a tablet comprising (a) 60 mg of Compound II (active ingredient); and (b) lactose monohydrate, microcrystalline cellulose, croscarmellose sodium, and magnesium stearate for the tablet core, and a tablet coating comprising polyvinyl alcohol-part hydrolyzed, titanium dioxide, polyethylene glycol 3350, and talc.

In an embodiment of the present invention, Compound I is contained in a solid molecular complex formed with hydroxypropyl methyl cellulose acetate succinate (HPMC-AS). In certain embodiments Compound I is present in the polymer in a final state of subdivision. In certain embodiments, Compound I is molecularly dispersed within the HPMC-AS matrix such that it is immobilized in its amorphous form. In some embodiments the polymer may prevent intramolecular hydrogen bonding or weak dispersion forces between two or more molecules of Compound I. In some embodiments the ratio of the amount by weight of Compound I within the solid molecular complex to the amount by weight of HPMC-AS therein is from about 1:9 to about 5:5. In an embodiment, said ratio is from about 2:8 to about 4:6. In another embodiment, said ratio is about 3:7.

In certain embodiments, compound I is provided in the aforementioned solid molecular complex of Compound I and HPMC-AS blended with colloidal silicon dioxide. In certain embodiments, the blend is at least 0.5% by weight silicon dioxide. In an embodiment of the present invention, the blend is about 97% complex and about 3% silicon dioxide.

In other embodiments, compound I is provided as a composition comprising the aforementioned solid molecular complex, either blended or not blended with silicon dioxide as described above, and a pharmaceutically acceptable carrier. In certain embodiments, the aforementioned complex or blend comprising the same is suspended in the carrier. An example of a carrier is hydroxypropylcellulose (HPC). In an embodiment, the vehicle contains about 2% by weight HPC. The composition may also contain additional agents such as preserving agents, solubilizing agents, stabilizing agents, wetting agents, emulsifying agents, sweetening agents, coloring agents, flavoring agents, salts for varying the osmotic pressure, buffers, coating agents and antioxidants. In certain embodiments, compound I is provided as a composition comprising a solid molecular complex of Compound I and HPMC-AS blended with colloidal silicon dioxide, hydroxypropylcellulose, Crospovidone (a disintegrating agent), magnesium stearate (a lubricant that may be used in tablet and capsulation operations), and/or croscarmellose sodium (a disintegrating agent). In an embodiment, Compound I is provided as a hard gelatin capsule comprising a solid molecular complex of Compound I and HPMC-AS blended with colloidal silicon dioxide, hydroxypropylcellulose, magnesium stearate, and croscarmellose sodium. In an embodiment, Compound I is provided as a tablet comprising Compound I, or a pharmaceutically acceptable salt thereof. In an embodiment, the tablet comprises a solid molecular complex of Compound I, or a pharmaceutically acceptable salt thereof, and HPMC-AS. The complex may, for example, be blended with colloidal silicon dioxide, hydroxypropylcellulose, magnesium stearate, and croscarmellose sodium. The tablet may, for example, be coated with a film coating. The film coating may, for example, comprise polyvinyl alcohol, titanium dioxide, polyethylene glycol 3350, talc, and iron oxide red. In some embodiments, Compound I is provided as a 240 mg tablet. Compositions comprising Compound I and methods of making such compositions are described in WO2010/114928 (which is hereby incorporated by reference in its entirety).

In some embodiments, Compound I or a pharmaceutically-acceptable salt thereof, is substantially in amorphous form. In some embodiments, Compound I, or a pharmaceutically-acceptable salt thereof, is in amorphous form. In some embodiments, Compound I, or a pharmaceutically-acceptable salt thereof, is contained in a solid molecular complex formed with hydroxypropyl methyl cellulose acetate succinate such that it is immobilized in its amorphous form. In some embodiments, Compound I, or a pharmaceutically-acceptable salt thereof, and hydroxypropyl methyl cellulose acetate succinate in said complex are in a ratio of from about 1:9 to about 5:5, respectively. In some embodiments, Compound I, or a pharmaceutically-acceptable salt thereof, and hydroxypropyl methyl cellulose acetate succinate in said complex are in a ratio of about 3:7, respectively. In some embodiments, Compound I is comprised in a blend wherein about 97% by weight of the blend is the solid molecular complex and about 3% by weight of the blend is silicon dioxide. In some embodiments, Compound I is comprised in a suspension of the solid molecular complex in a pharmaceutically acceptable carrier, wherein the solid molecule complex in a pharmaceutically acceptable carrier. In some embodiments, a first component comprises a tablet comprising a solid molecular complex of Compound I, or a pharmaceutically-acceptable salt thereof, and HPMC-AS. In some embodiments, Compound I is provided as a tablet. In some embodiments, Compound I is provided as a 240 mg tablet (i.e., a tablet comprising 240 mg of Compound I).

Administration of the therapeutic agents in combination typically is carried out over a defined time period (usually minutes, hours, days or weeks depending upon the combination selected). Combination therapy is intended to embrace administration of these therapeutic agents in a sequential manner, that is, wherein each therapeutic agent is administered at a different time (in any order), as well as administration of the therapeutic agents, in a concurrent (simultaneous) manner. Concurrent administration may be as separate pharmaceutical formulations or as a single dosage form (e.g., as a single pharmaceutical formulation. In some embodiments, Compound II is administered once a day, for example, in the morning or in the formulation). In some embodiments, Compound II is administered once a day at any time of day. In some embodiments, the second 960 mg dose (e.g., four 240 mg tablets) of Compound I is about 12 hours after the first 960 mg dose (e.g., four 240 mg tablets) of Compound I. In some embodiments, Compound I is administered once in the morning and once in the evening.

Thus, provision of compound I and II in a single dosage form is contemplated (e.g., co-formulation of two or more active ingredients). Accordingly, in one embodiment, a pharmaceutical composition herein may comprise more than one active compound (i.e., the first composition comprising a first active ingredient may be co-formulated with a second composition comprising a second active ingredient). Such molecules are suitably present in combination in amounts that are effective for the purpose intended.

In another aspect, each of two (or more) active ingredients is patiently formulated and administered as a separate dosage form. Accordingly, in some embodiments, a pharmaceutical product comprises a first composition comprising (as an active ingredient) Compound II; and a second composition comprising (as an active ingredient) Compound I, wherein the first composition is administered in a first dosage form, and the second composition is administered in a second dosage form. In some embodiments, the first composition is administered sequentially to the second composition. In some embodiments, the first composition is administered prior to the second composition. In some embodiments, the second composition is administered after the second composition. In some embodiments, the first composition is administered concurrently with the first composition.

The therapeutic agents are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In some embodiments, the administration is oral (in some embodiments, with or without food). In some embodiments, oral administration is with food. In some embodiments, oral administration is without food.

The therapeutic agent can be administered by the same route or by different routes. For example, one therapeutic agent in the combination may be administered by intravenous injection while another therapeutic agent inhibitor in the combination may be administered orally. Alternatively, for example, both of the therapeutic agents may be administered orally, or both therapeutic agents may be administered by intravenous injection, depending on the specific therapeutic agents. In some embodiments, Compound II and Compound I are administered orally. Compound II and Compound I may be orally administered with or without food. In some embodiments, Compound II is orally administered with or without food. In some embodiments, Compound I is orally administered with or without food.

III. Diagnostic Methods

In some embodiments, the patient herein is subjected to a diagnostic test e.g., prior to and/or during and/or after therapy.

In some aspects, methods are provided for selecting a therapy for a patient with unresectable or metastatic melanoma comprising determining presence (in some embodiments, presence or absence) of $BRAF^{V600}$ mutation in the patient's unresectable or metastatic melanoma sample, and selecting a cancer medicament based on the presence (in some embodiments, presence or absence) of $BRAF^{V600}$ mutation. In one embodiment, the sample is shown to express $BRAF^{V600}$ mutation (for example, $BRAF^{V600E}$ mutation), wherein treatment (e.g., therapeutic treatment) with Compound II in combination with Compound I is selected (e.g., as described herein). In some embodiments, the patient is treated (e.g., therapeutically treated) for unresectable or metastatic melanoma with a method comprising administering to the patient (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, on days 1-28 of the 28 day cycle. Treatment methods include any treatment methods herein. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

In other aspects, methods are provided for optimizing therapeutic efficacy comprising determining presence (in some embodiments, presence or absence) of $BRAF^{V600}$ mutation in a patient's unresectable or metastatic melanoma sample, and selecting a cancer medicament based on the presence (in some embodiments, presence or absence) of $BRAF^{V600}$ mutation. In one embodiment, the sample is shown to express $BRAF^{V600}$ mutation (for example, $BRAF^{V600E}$ mutation), wherein treatment with Compound II in combination with Compound I is selected (e.g., as described herein). In some embodiments, the patient is treated for unresectable or metastatic melanoma with a method comprising administering to the patient (i) Compound II, or a pharmaceutically acceptable salt thereof, at a dose of 60 mg, on days 1-21 of a 28 day cycle; and (ii) Compound I, or a pharmaceutically acceptable salt thereof, at a dose of 960 mg twice daily, on days 1-28 of the 28 day cycle. Treatment methods include any treatment methods herein. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

Methods for detection of BRAF and mutant BRAF are known in the art and are commercially available. See, e.g., Hailat et al, Diagn Mol Pathol. 2012 March; 21(1):1-8. In some embodiments, BRAF V600E mutation (also known as V599E (T1796A)) is detected using a method that comprises determining the presence of a single-base mutation (T to A) at nucleotide position 1799 in codon 600 of exon 15. This mutation can also result from the two-base mutation TG to AA at nucleotide positions 1799-1800. Other mutations also can occur at BRAF protein residue 600. These include V600K, V600D, and V600R.

In some embodiments, the presence of a V600 mutation may be determined by assessing BRAF nucleic acid, e.g., genomic DNA or mRNA, for the presence of a base substitution at position 1799. In some embodiments, the following V600 mutation is detected: V600K (GTG to AAG), V600R (GTG to AGG), V600E (GTG to GAA) and/or V600D (GTG to GAT), in all cases where the parenthesis refers to the nucleotide positions 1798-1800 of BRAF. In some embodiments, a mutant BRAF polynucleotide comprises the T1799A mutation.

Various methods for analyzing DNA (such as genomic DNA or cDNA) are known in the art, and include, but are not limited to, gene expression profiling, polymerase chain reaction (PCR) (including quantitative real time PCR (qRT-PCR), allele-specific PCR), sequencing, RNA-Seq, FISH, and/or microarray analysis. In some embodiments, a nucleic acid analytical method is one or more of: hybridization using allele-specific oligonucleotides, primer extension, allele-specific ligation, sequencing (including but not limited to Sanger sequencing, pyrosequencing), or electrophoretic separation techniques, e.g., singled-stranded conformational polymorphism (SSCP) and heteroduplex analysis, 5' nuclease assays, allele-specific PCR, template-directed dye-terminator incorporation, molecular beacon allele-specific oligonucleotide assays, single-base extension assays.

Analysis of amplified nucleic acid sequences can be performed using various technologies such as microchips, fluorescence polarization assays, and matrix-assisted laser desorption ionization (MALDI) mass spectrometry. In some embodiments, amplified nucleic acids are analyzed by sequencing. Two additional methods that can be used are assays based on invasive cleavage with Flap nucleases and methodologies employing padlock probes.

The COBAS® 4800 BRAF V600 Mutation Test is commercially available and utilizes real-time PCR technology. Each target-specific, oligonucleotide probe in the reaction is labeled with a fluorescent dye that serves as a reporter, and with a quencher molecule that absorbs (quenches) fluorescent emissions from the reporter dye within an intact probe. During each cycle of amplification, probe complementary to the single-stranded DNA sequence in the amplicon binds and is subsequently cleaved by the 5' to 3' nuclease activity of the Z05 DNA polymerase. Once the reporter dye is separated from the quencher by this nuclease activity, fluorescence of a characteristic wavelength can be measured when the reporter dye is excited by the appropriate spectrum of light. Two different reporter dyes are used to label the target-specific BRAF wild-type (WT) probe and the BRAF V600E mutation (MUT) probe. Amplification of the two BRAF sequences can be detected independently in a single reaction well by measuring fluorescence at the two characteristic wavelengths in dedicated optical channels.

In some embodiments, mutant BRAF polynucleotide (e.g., DNA) is detected using a method comprising (a) performing PCR on nucleic acid (e.g., genomic DNA) extracted from a patient cancer sample (such as a FFPE patient cancer sample); and (b) determining expression of mutant BRAF polynucleotide in the sample. In some embodiments, mutant BRAF polynucleotide expression is detected using a method comprising (a) hybridizing a first and second oligonucleotides to at least one variant of the BRAF target sequence; wherein said first oligonucleotide is at least partially complementary to one or more variants of the target sequence and said second oligonucleotide is at least partially complementary to one or more variants of the target sequence, and has at least one internal selective nucleotide complementary to only one variant of the target sequence; (b) extending the second oligonucleotide with a nucleic acid polymerase; wherein said polymerase is capable of extending said second oligonucleotide preferentially when said selective nucleotide forms a base pair with the target, and substantially less when said selective nucleotide does not form a base pair with the target; and (c) detecting the products of said oligonucleotide extension, wherein the extension signifies the presence of the variant of a target sequence to which the oligonucleotide has a complementary selective nucleotide. In some embodiments, mutant BRAF polynucleotide (e.g., DNA) is detected using a method comprising (a) performing PCR on nucleic acid (e.g., genomic DNA) extracted from a patient cancer sample (such as a FFPE fixed patient cancer sample); and (b) determining expression of mutant BRAF polynucleotide in the sample. In some embodiments, mutant BRAF polynucleotide (e.g., DNA) is detected using a method comprising (a) isolating DNA (e.g., genomic DNA) from a patient cancer sample (such as a FFPE patient cancer sample); (b) performing PCR on the DNA extracted from a patient cancer sample; and (c) determining expression of mutant BRAF polynucleotide in the sample.

In some embodiments, mutant BRAF polynucleotide expression is detected using a method comprising (a) isolating DNA (e.g., genomic DNA) from a patient cancer sample (such as a FFPE patient cancer sample); (b) hybridizing a first and second oligonucleotides to at least one variant of the BRAF target sequence in the DNA; wherein said first oligonucleotide is at least partially complementary to one or more variants of the target sequence and said second oligonucleotide is at least partially complementary to one or more variants of the target sequence, and has at least one internal selective nucleotide complementary to only one variant of the target sequence; (c) extending the second oligonucleotide with a nucleic acid polymerase; wherein said polymerase is capable of extending said second oligonucleotide preferentially when said selective nucleotide forms a base pair with the target, and substantially less when said selective nucleotide does not form a base pair with the target; and (d) detecting the products of said oligonucleotide extension, wherein the extension signifies the presence of the variant of a target sequence to which the oligonucleotide has a complementary selective nucleotide. In some embodiments, mutant BRAF polynucleotide expression is detected using a method comprising (a) hybridizing a first and second oligonucleotides to at least one variant of the BRAF target sequence; wherein said first oligonucleotide is at least partially complementary to one or more variants of the target sequence and said second oligonucleotide is at least partially complementary to one or more variants of the target sequence, and has at least one internal selective nucleotide complementary to only one variant of the target sequence; (b) extending the second oligonucleotide with a nucleic acid polymerase; wherein said polymerase is capable of extending said second oligonucleotide preferentially when said selective nucleotide forms a base pair with the target, and substantially less when said selective nucleotide does not form a base pair with the target; and (c) detecting the products of said oligonucleotide extension, wherein the extension signifies the presence of the variant of a target sequence to which the oligonucleotide has a complementary selective nucleotide.

In some embodiments, mutant BRAF polynucleotide (e.g., DNA) is detected using a method comprising (a) performing PCR on nucleic acid (e.g., genomic DNA) extracted from a patient cancer sample (such as a FFPE patient cancer sample); (b) determining expression of mutant BRAF polynucleotide by sequencing the PCR amplified nucleic acid. In some embodiments, mutant BRAF polynucleotide (e.g., DNA) is detected using sequencing (e.g., Sanger sequence or pyrosequencing).

In some embodiments, BRAF (e.g., BRAF$^{V600}$) protein expression is analyzed. Such protein analysis may be performed using immunohistochemistry (IHC), e.g., on patient tumor samples or proteomic methods.

A sample from the patient is tested for expression of one or more of the biomarkers herein. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the patient. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsies, tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples. In one embodiment, the patient sample is a formalin-fixed paraffin-embedded (FFPE) cancer sample (e.g., a unresectable or metastatic melanoma cancer sample). The sample may be obtained prior to the patient's treatment with a cancer medicament. The sample may be obtained from the primary tumor or from a metastatic tumor. The sample may be obtained when the cancer is first diagnosed and/or, for example, after the tumor has metastasized. In some embodiments, the metastasized tumor sample is of lung, skin, lymph node, bone, liver, colon, thyroid, and/or ovary.

IV. Articles of Manufacture

In another embodiment of the invention, an article of manufacture for use in treating cancer (such as BRAF$^{V600}$-positive unresectable or metastatic melanoma) is provided. The article of manufacture comprises a container and a label or package insert on or associated with the container. Suitable containers include, for example, bottles, vials, syringes, pill packs, blister packs, dial packs, etc. The containers may be formed from a variety of materials such as glass or plastic. The container holds or contains a composition comprising the cancer medicament (e.g., Compound II) as the active agent. In some embodiment, the composition comprising the cancer medicament is provided as a tablet. In some embodiments, the article of manufacture comprises a container and a tablet comprising 60 mg of Compound II. In some embodiments, the article of manufacture comprises a container and a tablet comprising 20 mg or 40 mg of Compound II. In some embodiments, article of manufacture comprising first container comprising (a) a first composition comprising Compound II (e.g., 60 mg of Compound II) provided as a tablet and (b) a second composition comprising Compound I (e.g., 960 mg of Compound I) provided as a tablet (e.g., four 240 mg tablets). In some embodiments, the container is a pill pack or a blister pack. In some embodiments, the first composition comprising Compound I and the second Composition comprising Compound II are provided as a single dosing form. In some embodiments, the first composition comprising Compound II and the second composition comprising Compound I are co-formulated (e.g., as a pharmaceutical formulation). In some embodiments, the article of manufacture (e.g., provided as a pill pack or a blister pack) comprises 21 tablets (e.g., of a composition comprising Compound II (e.g., tablets comprising 60 mg of Composition II; and tablets of a composition comprising Compound I (e.g., tablets comprising 240 mg of Compound I). In some embodiments, Compound II is provided as a 60 mg tablet. In some embodiments, Compound II is provided as a tablet comprising one or more of lactose monohydrate, microcrystalline cellulose, croscarmellose sodium, and magnesium stearate for the tablet core. In some embodiments, the tablet coating comprises one or more of polyvinyl alcohol-part hydrolyzed, titanium dioxide, polyethylene glycol 3350, and talc. In some embodiments, Compound II is provided as a tablet comprising of lactose monohydrate, microcrystalline cellulose, croscarmellose sodium, and magnesium stearate for the tablet core, and a tablet coating comprising polyvinyl alcohol-part hydrolyzed, titanium dioxide, polyethylene glycol 3350, and talc. In some embodiments, Compound II is provided as a tablet comprising (a) 60 mg of Compound II (active ingredient); and (b) lactose monohydrate, microcrystalline cellulose, croscarmellose sodium, and magnesium stearate for the tablet core, and a tablet coating comprising polyvinyl alcohol-part hydrolyzed, titanium dioxide, polyethylene glycol 3350, and talc.

The article of manufacture may further include a second container and/or other materials desirable from a commercial and user standpoint, including other buffers, diluents, filters, needles, and syringes.

The article of manufacture of the present invention also includes information, for example in the form of a package insert, indicating that, for example, Compound II is for treating (e.g., therapeutically treating) a patient with BRAF$^{V600}$ mutation-positive unresectable or metastatic melanoma, in combination with Compound I, wherein treatment comprises administering (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg (e.g., four 240 mg tablets) twice daily, on days 1-28 of the 28 day cycle. Treatment may, for example, increase survival of the patient, decrease the patient's risk of cancer recurrence and/or increase the patient's likelihood of survival. The insert or label may take any form, such as paper or on electronic media such as a magnetically recorded medium (e.g., floppy disk) or a CD-ROM. The label or insert may also include other information concerning the pharmaceutical compositions and dosage forms in the kit or article of manufacture. Treatment methods include any of the methods disclosed herein. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

The invention also concerns a method for manufacturing an article of manufacture comprising combining in a package a pharmaceutical composition comprising Compound II and a package insert indicating that the pharmaceutical composition is for treating (e.g., therapeutically treating) a patient with BRAF$^{V600}$ mutation-positive unresectable or metastatic melanoma, in combination with vemurafenib, wherein (i) a first composition comprising Compound II, or a pharmaceutically acceptable salt thereof, is administered at a dose of 60 mg, on days 1-21 of a 28 day cycle; and (ii) a second composition comprising Compound I, or a pharmaceutically acceptable salt thereof, is administered at a dose of 960 mg twice daily, on days 1-28 of the 28 day cycle. Treatment may, for example, increase survival of the patient, decrease the patient's risk of cancer recurrence, increase duration of response to treatment and/or increase the patient's likelihood of survival. In some embodiments, the unresectable or metastatic melanoma has not been previously treated (i.e., previously treated for unresectable or metastatic melanoma). Treatment methods include any of the methods disclosed herein. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

The article of manufacture may further include other materials desirable from a commercial and user standpoint, including other buffers, diluents, filters, needles, and syringes.

V. Kits

The invention concern kits comprising (i) a first composition comprising Compound II, or a pharmaceutically acceptable salt thereof; and (ii) a second composition comprising Compound I, or a pharmaceutically acceptable salt thereof; for use in the treatment of unresectable or metastatic melanoma, wherein the compound II is administered at a dose of 60 mg, on days 1-21 of a 28 day cycle, and wherein compound I is administered at a dose of 960 mg (e.g., four 240 mg tablets), twice daily each day of the 28 day cycle. The kit may further comprise a package insert indicating that the pharmaceutical composition is for treating (e.g., therapeutically treating) a patient with $BRAF^{V600}$ mutation-positive unresectable or metastatic melanoma, in combination with vemurafenib, wherein (i) a first composition comprising Compound II, or a pharmaceutically acceptable salt thereof, is administered at a dose of 60 mg, on days 1-21 of a 28 day cycle; and (ii) a second composition comprising Compound I, or a pharmaceutically acceptable salt thereof, is administered at a dose of 960 mg (e.g., four 240 mg tablets) twice daily, on days 1-28 of the 28 day cycle. Treatment may, for example, increase survival of the patient, decrease the patient's risk of cancer recurrence, increase duration of response to treatment and/or increase the patient's likelihood of survival. In some embodiments, the unresectable or metastatic melanoma has not been previously treated (i.e., previously treated for unresectable or metastatic melanoma). In some embodiments, the unresectable or metastatic melanoma has not been previously treated. In some embodiments, the patient's unresectable or metastatic melanoma has been previously treated (in some embodiments, without prior treatment to BRAF inhibitor). In some embodiments, the first composition comprising Compound II is a tablet. In some embodiments, the second composition comprising Compound I is a tablet. In some embodiments, the first composition comprising Compound II and the first composition comprising Compound I are each provided as a tablet. In some embodiments, the first composition comprising Compound I and the second composition comprising Compound II are provided as a single dosing form. In some embodiments, the first composition comprising Compound II and the second composition comprising Compound I are co-formulated (e.g., as a pharmaceutical formulation). Treatment methods include any of the methods disclosed herein.

The invention also concerns diagnostic kits useful for detecting any one or more of the biomarker(s) identified herein. Accordingly, a diagnostic kit is provided which comprises one or more reagents for determining expression of BRAF expression, such as expression of $BRAF^{V600}$ biomarker in a sample from a cancer patient. Optionally, the kit further comprises instructions to use the kit if the patient's unresectable or metastatic melanoma expresses $BRAF^{V600}$, to select a composition comprising Compound II in combination with a composition comprising Compound I for treating (e.g., therapeutically treating) the patient, wherein treatment comprises administering (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, on days 1-28 of the 28 day cycle. In some embodiments, the patient's unresectable or metastatic melanoma has not been previously treated. In some embodiments, the patient's unresectable or metastatic melanoma has been previously treated (in some embodiments, without prior treatment to BRAF inhibitor). Treatment methods include any of the methods disclosed herein.

VI. Methods of Advertising

The invention herein also concerns a method for promoting or advertising a cancer medicament comprising promoting, to a target audience, the use of Compound II for treating (e.g., therapeutically treating) a patient with $BRAF^{V600}$ mutation-positive unresectable or metastatic melanoma, in combination with vemurafenib, wherein treatment comprises administering (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg twice daily, on days 1-28 of the 28 day cycle. Treatment may, for example, increase survival of the patient, decrease the patient's risk of cancer recurrence, increase duration of response to treatment and/or increase the patient's likelihood of survival. In some embodiments, the unresectable or metastatic melanoma has not been previously treated. In some embodiments, the patient's unresectable or metastatic melanoma has been previously treated (in some embodiments, without prior treatment to BRAF inhibitor). Advertising is generally paid communication through a non-personal medium in which the sponsor is identified and the message is controlled. Advertising for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The advertising and promotion of the diagnostic method herein may be accomplished by any means. Examples of advertising media used to deliver these messages include television, radio, movies, magazines, newspapers, the internet, and billboards, including commercials, which are messages appearing in the broadcast media. Advertisements also include those on the seats of grocery carts, on the walls of an airport walkway, and on the sides of buses, or heard in telephone hold messages or in-store PA systems, or anywhere a visual or audible communication can be placed.

More specific examples of promotion or advertising means include television, radio, movies, the internet such as webcasts and webinars, interactive computer networks intended to reach simultaneous users, fixed or electronic billboards and other public signs, posters, traditional or electronic literature such as magazines and newspapers, other media outlets, presentations or patient contacts by, e.g., e-mail, phone, instant message, postal, courier, mass, or carrier mail, in-person visits, etc.

The type of advertising used will depend on many factors, for example, on the nature of the target audience to be reached, e.g., hospitals, insurance companies, clinics, doctors, nurses, and patients, as well as cost considerations and the relevant jurisdictional laws and regulations governing advertising of medicaments and diagnostics. The advertising may be patientized or customized based on user characterizations defined by service interaction and/or other data such as user demographics and geographical location.

In some embodiments, the promotion is by a package insert where the package insert provides instructions to receive treatment with Compound II in combination with Compound I for treating (e.g., therapeutically treating) the patient, wherein treatment comprises administering (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg (e.g., four 240 mg tablets) twice daily, on days 1-28 of the 28 day cycle. In some embodiments, the promotion is followed by the treatment of the patient with the Compound II with or without the Compound I. In some embodiments, the package insert indicates that the Compound II is to be used to treat the patient if the patient's unresectable or recurrent metastatic melanoma sample is $BRAF^{V600}$ mutation positive. Treatment may, for example, increase survival of the patient, decrease the patient's risk of cancer recurrence, increase duration of response to treatment and/or increase the patient's likelihood of survival. Treatment methods include any of the methods disclosed herein. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

The invention also provides business methods, comprising marketing the use of Compound II for treating (e.g., therapeutically treating) a patient with $BRAF^{V600}$ mutation-positive unresectable or metastatic melanoma, in combination with Compound I, wherein treatment comprises administering (i) a first composition comprising Compound II, or a pharmaceutically acceptable salt thereof, at a dose of 60 mg, on days 1-21 of a 28 day cycle; and (ii) a second composition comprising Compound I, or a pharmaceutically acceptable salt thereof, at a dose of 960 mg (e.g., four 240 mg tablets) twice daily, on days 1-28 of the 28 day cycle. Treatment may, for example, increase survival of the patient, decrease the patient's risk of cancer recurrence, increase duration of response to treatment and/or increase the patient's likelihood of survival. Treatment methods include any of the methods disclosed herein. In some embodiments, the patient's unresectable or metastatic melanoma has not been previously treated (e.g., with vemurafenib or with BRAF inhibitor). In some embodiments, the patient's unresectable or metastatic melanoma has been previously treated (in some embodiments, without prior treatment to BRAF inhibitor).

EXAMPLES

The following are examples of methods and compositions of the invention. It is understood that various other embodiments may be practiced, given the general description provided above.

Example 1

Study NO25395 (BRIM-7) is a Phase Ib study designed to assess the safety, tolerability, and pharmacokinetics of the combination of (a) MEK inhibition with GDC-0973, and (b) BRAF inhibition with vemurafenib. This multicenter study has 2 stages: a dose-escalation stage and a cohort-expansion stage.

This study is being conducted in patients with $BRAF^{V600}$ mutation-positive, unresectable locally advanced or metastatic melanoma who are either vemurafenib naïve (previously untreated or previously treated but without prior exposure to BRAF therapy) or have progressed on vemurafenib treatment immediately prior to enrollment in this study. Key inclusion criteria include the presence of the V600E mutation in melanoma tumor tissue using the Cobas® 4800 BRAF V600 mutation test, measurable disease per Response Evaluation Criteria in Solid Tumors (RECIST) v1.1, ECOG PS of ≤1, and adequate hematologic and end organ function as assessed through key laboratory measures. Patients were excluded if they had: ocular pathology or risk factors that predisposes to retinal vein occlusion; QTc >450 ms; or active CNS metastasis. Patients treated with stereotactic radiation therapy or surgery were eligible if stable for ≥3 weeks prior to treatment.

All patients in the dose-escalation stage received twice daily vemurafenib in combination with GDC-0973 administered daily according to one of the following 28-day schedules: 14 consecutive days of study drug followed by a 14-day drug holiday (14/14), 21 consecutive days of study drug followed by a 7-day drug holiday (21/7), or as a continuous daily dose (28/0). Each treatment cycle was 28 days.

There were 10 dose-escalation cohorts of 3-6 patients per cohort (FIG. 1). Patients in Cohort 1 received vemurafenib at a dose of 720 mg BID continuously and GDC-0973 60 mg once daily (QD) for 14 consecutive days of each 28-day cycle of combination dosing (14/14). Dose-escalation used the standard 3+3 design and proceeded in increments, taking into account the safety and tolerability of the combination.

Results

As of 20 Sep. 2012, a total of 92 patients received at least one dose of combination treatment with vemurafenib and GDC-0973. The following dose-levels were deemed safe and tolerable:

Vemurafenib 720 mg BID+GDC-0973 60 mg QD 14/14 (Cohort 1)

Vemurafenib 720 mg BID+GDC-0973 80 mg QD 14/14 (Cohort 2)

Vemurafenib 960 mg BID+GDC-0973 60 mg QD 14/14 (Cohort 3)

Vemurafenib 720 mg BID+GDC-0973 60 mg QD 21/7 (Cohort 1A)

Vemurafenib 960 mg BID+GDC-0973 60 mg QD 21/7 (Cohort 1B)

Vemurafenib 720 mg BID+GDC-0973 60 mg QD 28/0 (Cohort 1C)

Vemurafenib 960 mg BID+GDC-0973 80 mg QD 14/14 (Cohort 4)

Vemurafenib 720 mg BID+GDC-0973 100 mg QD 14/14 (Cohort 2A)

(BID=twice daily; QD=once daily)

Eligible patients had BRAF$^{V600}$-mutated unresectable or metastatic melanoma, and ECOG PS 0-1. Patients were either naïve to vemurafenib or had disease progression on vemurafenib. The study consisted of dose-escalation and expansion stages. Patients received vemurafenib at 720 mg or 960 mg BID (twice daily) each day of a 28 day cycle. GDC-0973 was administered at doses of 60 mg, 80 mg or 100 mg QD (once daily) 14 days (d) on/14 d off (14/14); 21 d on/7 d off (21/7); or each day of a 28 day cycle. Primary endpoints were maximum tolerated dose (MTD), dose-limiting toxicity (DLT) of both drugs, safety, and PK.

FIG. 3 shows patient characteristics as of 6 Jul. 2012. Seventy patients (70% male; median age: 57.5 years [range: 19-76]; 74.3% Stage IV M1c, 54.5% had previously progressed on vemurafenib) received greater than or equal to one dose of GDC-0973+vemurafenib. Median number of cycles was three.

As of 18 Sep. 2012, dose-limiting toxicity was observed in three patients: Grade 3 QT prolongation related to vemurafenib, leading to discontinuation of vemurafenib (cohort 1B), Grade 3 mucositis related to vemurafenib and GDC-0973 (cohort 1D), and Grade 3 arthralgia related to vemurafenib (cohort 1D).

FIG. 4 shows adverse events attributed to either vemurafenib or GDC-0973 in all patients as of 6 Jul. 2012. Most common adverse events for all patients were diarrhea (51.4%), non-acneiform rash (52.9%), nausea (28.6%), fatigue (30.0%), and photosensitivity/sunburn (31.4%). Additive toxicity was not observed with the addition of GDC-0973 to vemurafenib. Twenty percent of patients showed liver function test elevation, which were mostly mild (grade 1 or 2). Only 4.3% of patients showed Grade 3 or 4 liver function test elevation. Arthralgia was observed in 12.9% of patients and this is within the range observed with vemurafenib treatment alone. Serous choreoretinopathy was observed in three patients, with all cases being mild. Only one patient developed cutaneous squamous cell carcinoma out of 70 patients treated with vemurafenib and GDC-0973. Thus, the frequency of squamous cell carcinoma appeared to be lower than that observed with treatment with vemurafenib alone. This finding is consistent with the mechanism of development of squamous cell carcinoma lesions via paradoxical activation of the MAPK pathway. Most frequent treatment-related Grade ≥3 adverse events were diarrhea (5.7%), increased creatine phosphokinase (4.5%), alkaline phosphatase elevation (4.5%) and maculopapular rash (4.5%).

FIG. 5 shows adverse events that led to dose interruptions, reductions and permanent discontinuations as of 6 Jul. 2012. Most common reasons for temporary interruption of vemurafenib were: rash (8 patients), liver function test (LFT) abnormalities (3 patients) and arthralgia (3 patients). Most common reasons for temporary interruption of GDC-0973 were: rash (5 patients) and diarrhea (3 patients). Reasons for primary dose reduction interruption of vemurafenib were: LFT abnormality (1 patient), central serous retinopathy (1 patient) and rash (1 patient). Reasons for primary dose reduction interruption of GDC-0973 were: central serous retinopathy (1 patient) and rash (1 patient). Reason for discontinuation of vemurafenib was: QT interval prolongation (1 patient). Only a small number of patients required dose reductions or permanent discontinuations. These results support the conclusion that the combination was well tolerated in the tested patients.

Two dose levels were selected for expansion: vemurafenib (720 mg & 960 mg BID)+GDC-0973 60 mg QD 21/7.

Figure 6:
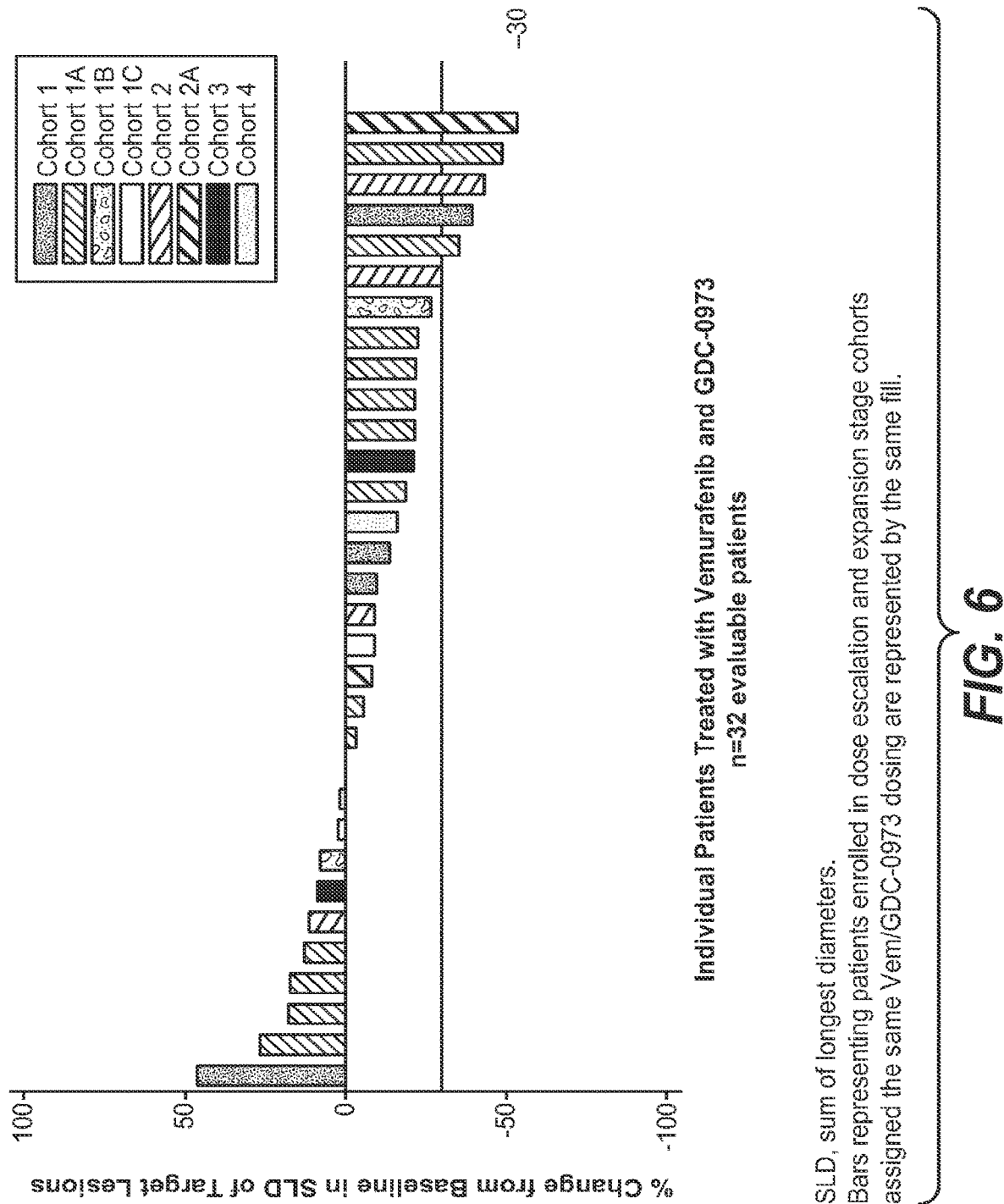
FIG. 6: shows change in tumor size from baseline to best response in patients who progressed on prior vemurafenib.

FIG. 6 shows the change in tumor size from baseline to best response in patients who progressed on prior vemurafenib. Treatment with the combination in patients who progressed on prior vemurafenib treatment was not associated with a significant tumor response.

Figure 7:
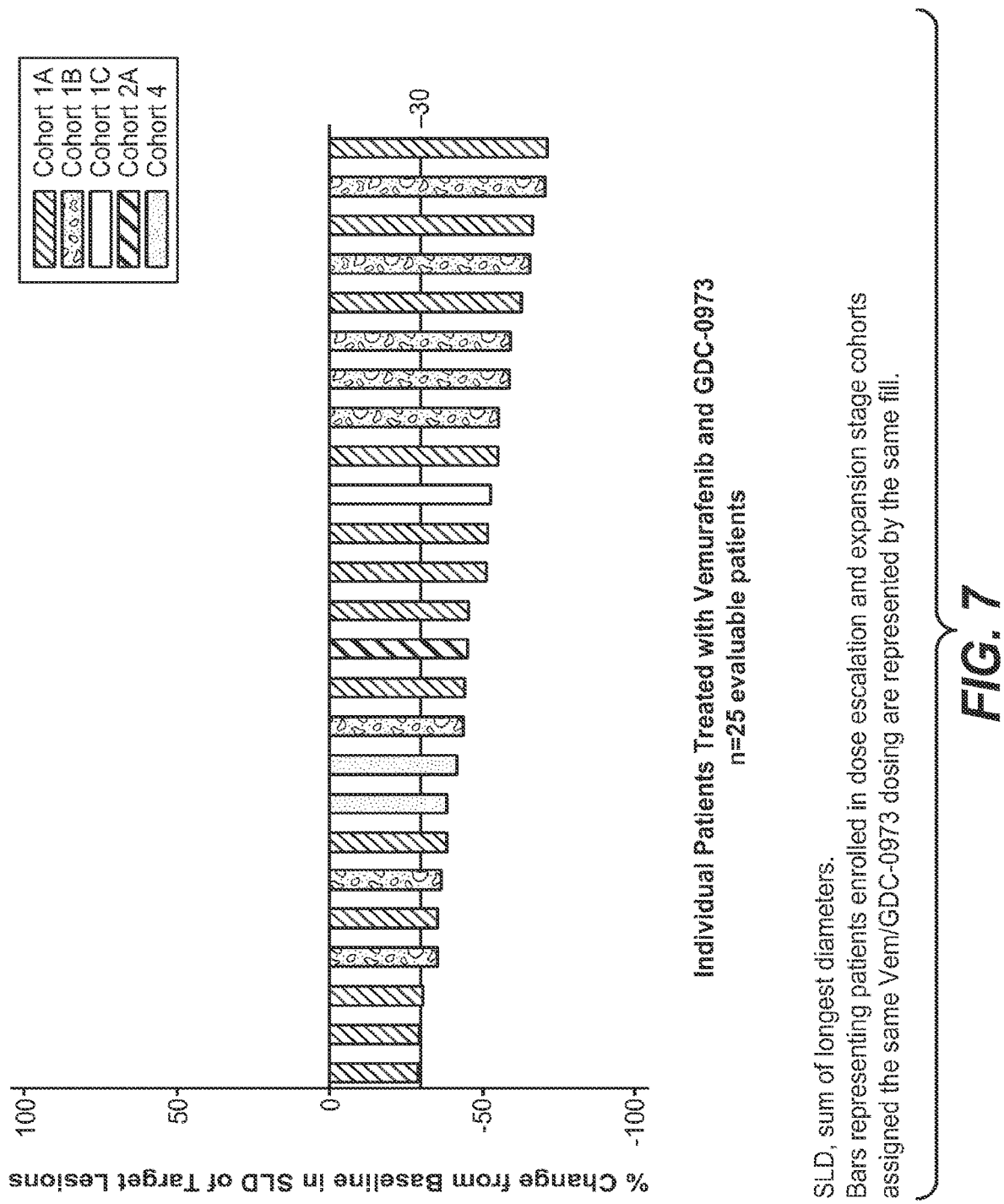
FIG. 7: shows change in tumor size from baseline to best response in vemurafenib-naïve patients.

FIG. 7 shows change in tumor size from baseline to best response in vemurafenib-naïve patients. Preliminary efficacy data in 25 vemurafenib-naïve patients showed that all 25 patients had tumor reduction. The confirmed response rate per RECIST 1.1 criteria in vemurafenib-naïve patients is 40%, and stable disease rate is 60%.

Figure 8B:
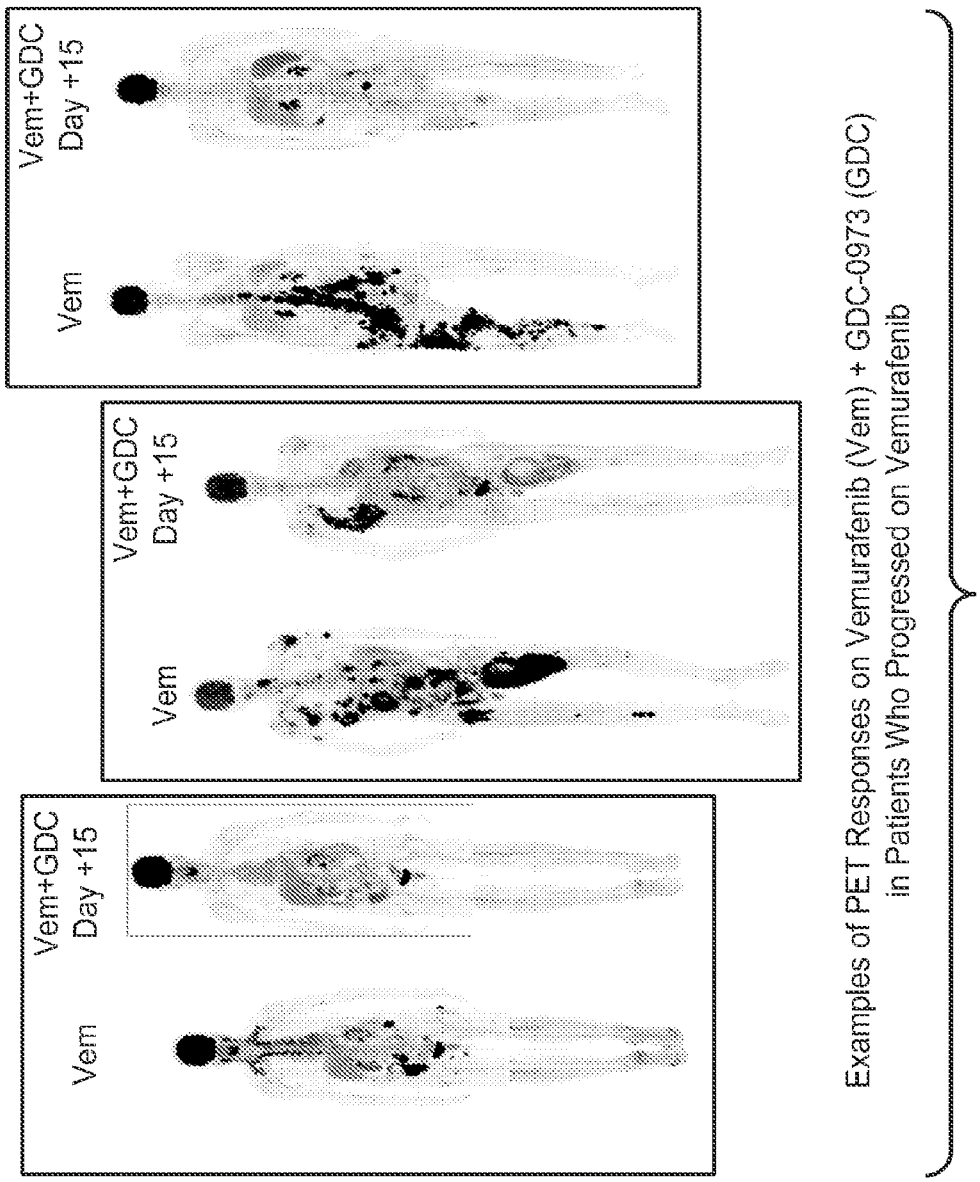
FIGS. 8A & B: A. PET scan response in a patient who had progressed on prior vemurafenib treatment and following treatment with vemurafenib+GDC-0973. B. Additional examples of PET responses in patients who had progressed on prior vemurafenib treatment who were treated with vemurafenib+GDC-0973 (GDC).
Figure 8A:
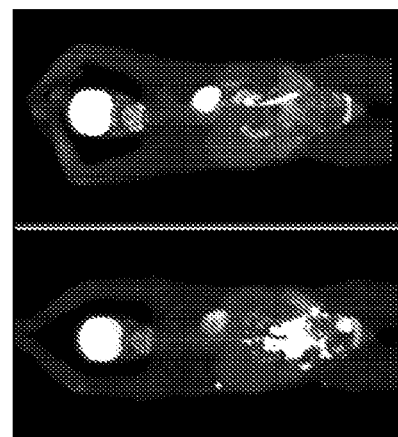

FIG. 8A shows PET scan response in a patient who had progressed on prior vemurafenib treatment after treatment with vemurafenib+GDC-0973. A significant reduction in PET activity was observed on day 14 of combination treatment. This result demonstrated that treatment with the combination of vemurafenib and GDC-0973 was able to rapidly reverse vemurafenib resistance. FIG. 8B shows additional examples of PET responses in patients who had progressed on prior vemurafenib treatment who were treated with vemurafenib (Vem)+GDC-0973 (GDC).

These results demonstrated that GDC-0973 in combination with vemurafenib was tolerable and adverse events were manageable. The combination was delivered safely at the respective single-agent MTDs of vemurafenib (960 mg BID) and GDC-0973 (60 mg 21/7). Pharmacokinetic data from the study showed that vemurafenib and GDC-0973 exposures were similar to those observed previously in single-agent studies. No significant PK interactions were observed between vemurafenib and GDC-0973.

Example 2

Treatment with vemurafenib 960 mg BID (twice daily) on Days 1-28 and GDC-0973 60 mg QD (once daily) Days 1-21, in 28-day treatment cycles was demonstrated to be safe and well tolerated. G028141 is a multicenter, randomized, double-blind, placebo-controlled Phase III clinical study to evaluate the safety and efficacy of vemurafenib in combination with GDC-0973 with vemurafenib alone, in previously untreated BRAF$^{V600}$ mutation-positive patients with unresectable locally advanced or metastatic melanoma.

Approximately 500 previously untreated BRAF$^{V600}$ mutation-positive patients with unresectable locally advanced or metastatic melanoma will be randomized in a 1:1 ratio to receive treatment with one of the following regimens:

Arm A (control arm): vemurafenib 960 mg by mouth (PO) BID on Days 1-28 and placebo PO QD on Days 1-21 of each 28-day treatment cycle.

Arm B (investigational arm): vemurafenib 960 mg PO BID on Days 1-28 and GDC-0973 60 mg PO QD on Days 1-21 of each 28-day treatment cycle.

BID=twice daily; QD=once daily.

The stratified, permuted-block randomization scheme will be used for treatment allocation based on the following stratification factors:

Geographic region (North America, Europe, Australia/New Zealand, or others).

Metastatic classification (unresectable stage IIIc, M1a, and M1b; or M1c).

Figure 2:
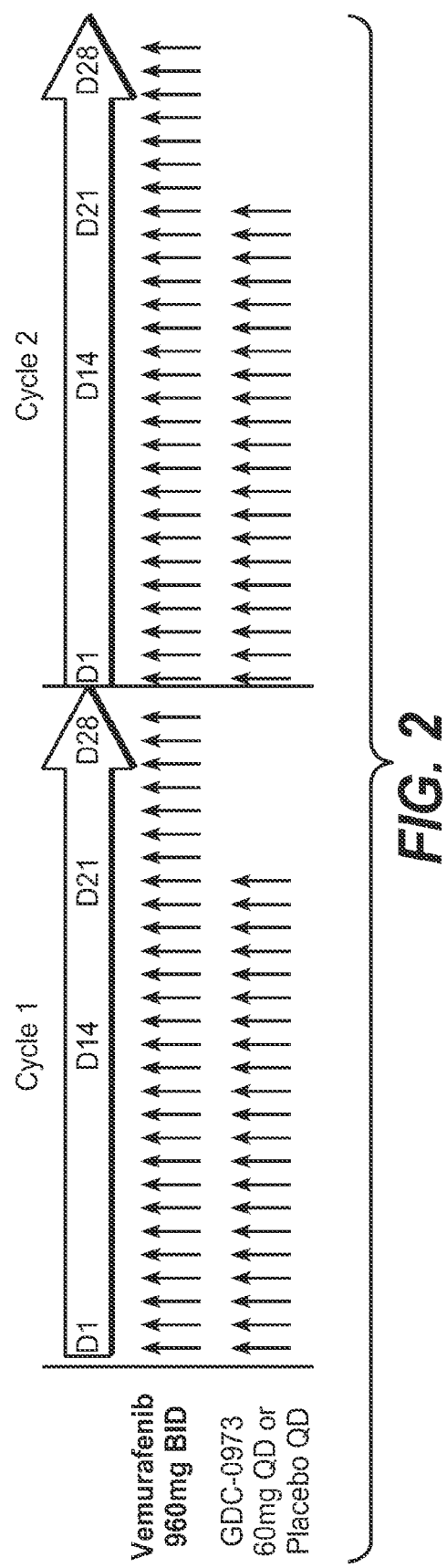
FIG. 2: shows the dosing scheme for vemurafenib and GDC-0973 or placebo. Two cycles of dosing are depicted.

FIG. 2 shows the dosing scheme for vemurafenib and GDC-0973/placebo in the study.

All patients are closely monitored for safety and tolerability during all cycles of therapy, at the end-of-study treatment visit, and during the follow-up period. Patients are assessed for adverse events every 2 weeks during the first 2 cycles, then prior to each subsequent cycle, and as necessary.

Tumor response is evaluated according to RECIST v1.1. Any evaluable and measurable disease is documented at screening and re-assessed at each subsequent tumor evaluation. Response is assessed by the investigator at 8-week intervals. At the investigator's discretion, CT/MRI scans are repeated at any time if progressive disease is suspected.

The NCI Common Terminology Criteria for Adverse Events (CTCAE) v4.0 is used to characterize the toxicity profile of the study treatments on all patients. ECG assessments are performed on Day 15 of the first 3 cycles and then on Day 15 every 3 treatment cycles thereafter (Cycles 6, 9, 12, etc.). Dermatologic assessment are performed at the beginning of Cycle 2 (±1 week) and then every 3 treatment cycles (±1 week) thereafter (Cycles 5, 8, 11, etc.). Ophthalmologic examinations are repeated if clinically indicated.

Patients are treated until disease progression, death, unacceptable toxicity, or withdrawal of consent, whichever occurs earliest. Patients on the vemurafenib and placebo treatment arm are not eligible to cross over to the vemurafenib and GDC-0973 treatment arm at disease progression and are followed for survival.

The primary efficacy objective of this study is to evaluate the efficacy of vemurafenib in combination with GDC-0973, compared with vemurafenib and placebo, in previously untreated BRAF$^{V600}$ mutation-positive patients with unresectable locally advanced or metastatic melanoma, as measured by prolongation of PFS, as assessed by the study site investigator.

The secondary efficacy objectives of this study is to evaluate the efficacy of vemurafenib in combination with GDC-0973, compared with vemurafenib and placebo, in previously untreated BRAF$^{V600}$ mutation-positive patients with unresectable locally advanced or metastatic melanoma, as measured by objective response rate (ORR), duration of response (DOR), and overall survival (OS).

The safety objective of this study is to characterize the toxicity profile in patients receiving vemurafenib and GDC-0973 versus vemurafenib and placebo. The pharmacokinetic objective of this study is to characterize the pharmacokinetics of GDC-0973 and vemurafenib and to compare the pharmacokinetics of vemurafenib when administered with GDC-0973 to the pharmacokinetics of vemurafenib when administered with placebo. The patient-reported outcome objective of this study is to evaluate health-related quality of life in patients receiving vemurafenib and GDC-0973 versus vemurafenib and placebo as measured by the European Organization for Research and Cancer (EORTC) Quality of Life Questionnaire and the EuroQol 5 dimension (EQ-5D) questionnaire.

Patients

To be eligible for this study, patients are previously untreated for unresectable locally advanced or metastatic melanoma. Patients have the BRAF$^{V600}$ mutation confirmed on their melanoma tumor tissue. A non-limiting list of inclusion and exclusion criteria includes:

Disease-Specific Inclusion Criteria:
Patients with histologically confirmed melanoma, either unresectable stage IIIc or stage IV metastatic melanoma, as defined by AJCC 7th edition.

Patients are naïve to treatment for locally advanced unresectable or metastatic disease (i.e., no prior systemic anti-cancer therapy for advanced disease; stage IIIc and IV). Prior adjuvant immunotherapy (including ipilimumab) is allowed.

Documentation of BRAF$^{V600}$ mutation-positive status in melanoma tumor tissue (archival or newly obtained tumor samples).

Measurable disease per RECIST v1.1

Cancer-Related Exclusion Criteria:
History of prior RAF or MEK pathway inhibitor treatment.

Palliative radiotherapy within 14 days prior to the first dose of study treatment.

Major surgery or traumatic injury within 14 days prior to first dose of study treatment.

Active malignancy other than melanoma that could potentially interfere with the interpretation of efficacy measures. Patients with a previous malignancy within the past 3 years are excluded except for patients with resected BCC or SCC of the skin, melanoma in-situ, carcinoma in-situ of the cervix, and carcinoma in-situ of the breast.

History of isolated elevation in prostate-specific antigen in the absence of radiographic evidence of metastatic prostate cancer is allowed.

GDC-0973 and Placebo

GDC-0973 is supplied as 20 mg tablets for oral use. GDC-0973 is packaged in blister packs. GDC-0973 placebo is packaged in blister packs identical to the GDC-0973 packs. The inactive ingredients in GDC-0973 are as follows: lactose monohydrate, microcrystalline cellulose, croscarmellose sodium, and magnesium stearate for the tablet core. The tablet coating consists of polyvinyl alcohol-part hydrolyzed, titanium dioxide, polyethylene glycol 3350, and talc. Placebo for GDC-0973 consists of all inactive ingredients listed above and is identical in appearance to GDC-0973.

Vemurafenib

Vemurafenib is supplied as 240 mg tablets for oral use. Vemurafenib is packaged in bottles. The inactive ingredients in vemurafenib tablets are as follows: hypromellose acetate succinate, croscarmellose sodium, colloidal silicon dioxide, magnesium stearate, hydroxypropyl cellulose (tablet core), polyvinyl alcohol, titanium dioxide, polyethylene glycol 3350, talc, and iron oxide red (tablet coating).

BRAF$^{V600}$ Mutation Testing

Patients whose melanoma tumors test positive for the BRAF$^{V600}$ mutation on the Cobas® 4800 BRAF V600 mutation test are eligible for enrollment in the clinical study if other eligibility criteria are met. Tumor samples may be obtained from the primary melanoma tumor or any metastatic site, as long as the requirements below are met. In some embodiments, archival or newly obtained formalin-fixed paraffin-embedded (FFPE) tumor specimens are utilized for the Cobas® 4800 BRAF V600 mutation test. In some embodiments, tumor specimens are collected as fresh frozen tissues, but tissues obtained from fine needle aspirations (FNA) are not permitted.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for extending duration of response to treatment in a patient having BRAFV600 mutation-positive unresectable or metastatic melanoma comprising administering to the patient (i) a first composition comprising [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof, at a dose of 60 mg on days 1-21 of a 28 day cycle; and (ii) a second composition comprising propane-1-sulfonic acid {3-[5-(4-chlorophenyl)-1H-pyrrolo[2,3-b]pyridine-3-carbonyl]-2,4-difluoro-phenyl}-amide, or a pharmaceutically acceptable salt thereof, at a dose of 960 mg twice daily on each day of the 28 day cycle.

2. The method of claim 1, wherein the BRAFV600 mutation-positive unresectable or metastatic melanoma was previously untreated.

3. The method of claim 1, wherein the BRAFV600 mutation-positive unresectable or metastatic melanoma is metastatic melanoma.

4. The method of claim 1, wherein BRAFV600 mutation is determined using a method comprising (a) performing PCR or sequencing on nucleic acid extracted from a sample of the patient's melanoma; and (b) determining expression of BRAFV600 in the sample.

5. The method of claim 1, wherein the [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof, is administered as a 20 mg tablet, as a 40 mg tablet, or as a 60 mg tablet.

6. A method of delaying or preventing development of resistance to treatment in a patient having BRAFV600 mutation-positive unresectable or metastatic melanoma comprising administering to the patient (i) a first composition comprising [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof, at a dose of 60 mg on days 1-21 of a 28 day cycle; and (ii) a second composition comprising propane-1-sulfonic acid {3-[5-(4-chlorophenyl)-1H-pyrrolo[2,3-b]pyridine-3-carbonyl]-2,4-difluoro-phenyl}-amide, or a pharmaceutically acceptable salt thereof, at a dose of 960 mg twice daily on each day of the 28 day cycle.

7. The method of claim 6, wherein the BRAFV600 mutation-positive unresectable or metastatic melanoma was previously untreated.

8. The method of claim 7, wherein the BRAFV600 mutation-positive unresectable or metastatic melanoma is metastatic melanoma.

9. The method of claim 6, wherein BRAFV600 mutation is determined using a method comprising (a) performing PCR or sequencing on nucleic acid extracted from a sample of the patient's melanoma; and (b) determining expression of BRAFV600 in the sample.

10. The method of claim 6, wherein the [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof, is provided as a 20 mg tablet, as a 40 mg tablet, or as a 60 mg tablet.

11. A kit comprising (i) a first composition comprising [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof; and (ii) a second composition comprising propane-1-sulfonic acid {3-[5-(4-chlorophenyl)-1H-pyrrolo[2,3-b]pyridine-3-carbonyl]-2,4-difluoro-phenyl}-amide, or a pharmaceutically acceptable salt thereof.

12. The kit of claim 6, further comprising a package insert indicating that the first and second compositions are for use in treating a patient with BRAFV600 mutation-positive unresectable or metastatic melanoma, wherein (i) the first composition is administered at a [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof, dose of 60 mg on days 1-21 of a 28 day cycle; and (ii) the second composition is administered at a propane-1-sulfonic acid {3-[5-(4-chlorophenyl)-1H-pyrrolo[2,3-b]pyridine-3-carbonyl]-2,4-difluoro-phenyl}-amide provided as a tablet, or a pharmaceutically acceptable salt thereof, dose of 960 mg twice daily on days 1-28 of the 28 day cycle.

13. The kit of claim 12, wherein the package insert further indicates that the BRAFV600 mutation-positive unresectable or metastatic melanoma was previously untreated.

14. The kit of claim 12, wherein the BRAFV600 mutation-positive unresectable or metastatic melanoma is metastatic melanoma.

15. The kit of claim 11, wherein the [3,4-difluoro-2-[(2-fluoro-4-iodophenyl)amino]phenyl][3-hydroxy-3-[(2S)-2-piperidinyl]-1-azetidinyl]methanone, or a pharmaceutically acceptable salt thereof, is provided as a 20 mg tablet, as a 40 mg tablet, or as a 60 mg tablet.

* * * * *

UNITED STATES PATENT AND TRADEMARK OFFICE
CERTIFICATE OF CORRECTION

| | |
|---|---|
| PATENT NO. | : 11,783,366 B2 |
| APPLICATION NO. | : 17/444691 |
| DATED | : October 10, 2023 |
| INVENTOR(S) | : Gordon Bray and Iris Chan |

It is certified that error appears in the above-identified patent and that said Letters Patent is hereby corrected as shown below:

In the Claims

In Claim 12, Column 36, Line 21, delete "claim 6," and insert therefor -- claim 11, --.

Signed and Sealed this
Twenty-sixth Day of March, 2024

Katherine Kelly Vidal
*Director of the United States Patent and Trademark Office*